United States Patent [19]
Jensen

[11] Patent Number: 4,821,709
[45] Date of Patent: Apr. 18, 1989

[54] HIGH FREQUENCY VENTILATOR AND METHOD

[75] Inventor: Robert L. Jensen, San Antonio, Tex.

[73] Assignee: SensorMedics Corporation, Anaheim, Calif.

[21] Appl. No.: 168,618

[22] Filed: Mar. 8, 1988

Related U.S. Application Data

[63] Continuation of Ser. No. 16,470, Feb. 17, 1987, abandoned, which is a continuation of Ser. No. 728,146, Apr. 29, 1985, abandoned, which is a continuation of Ser. No. 519,387, Aug. 1, 1983, abandoned, which is a continuation-in-part of Ser. No. 485,900, Apr. 18, 1983, abandoned, which is a continuation-in-part of Ser. No. 358,648, Mar. 16, 1982, abandoned.

[51] Int. Cl.⁴ ............... A61H 31/00; A61M 16/00
[52] U.S. Cl. ................. 128/204.21; 128/205.11
[58] Field of Search ............... 128/39, 204.12, 204.21, 128/204.23, 205.18, 205.19, 205.11

[56] References Cited

U.S. PATENT DOCUMENTS

| | | | |
|---|---|---|---|
| 2,918,917 | 12/1959 | Emerson | 128/202 |
| 4,001,700 | 1/1977 | Cook et al. | 328/129 |
| 4,036,221 | 7/1977 | Hillsman et al. | 128/145.6 |
| 4,155,356 | 5/1979 | Venegas | 128/145.6 |
| 4,215,681 | 8/1980 | Zalkin et al. | 128/204.21 |
| 4,340,044 | 7/1989 | Levy et al. | 128/204.4 |

OTHER PUBLICATIONS

Instrument Development Corporation, "High Frequency Jet Ventilation with the Model VS600".

*Primary Examiner*—Edward M. Coven
*Attorney, Agent, or Firm*—Cox & Smith Incorporated

[57] ABSTRACT

A high frequency ventilator which generates a high frequency pressure wave in a supply of ventilating gas for supporting ventilation in air breathing animals. The high frequency pressure wave causes the ventilating gas to be exchanged and to diffuse through the animal's lungs fast enough to support ventilation without spontaneous breathing on the part of the animal and without the aid of a separate ventilator.

56 Claims, 11 Drawing Sheets

HIGH FREQUENCY VENTILATOR AND METHOD

CROSS REFERENCE TO RELATED APPLICATIONS

This application is a continuation of co-pending application Ser. No. 016.470, abandoned filed on Feb. 17, 1987, which is a continuation of co-pending application Ser. No. 728,146, abandoned filed on Apr. 29, 1985, which is a continuation of co-pending application Ser. No. 519,387, abandoned filed Aug. 1, 1983, which is a continuation-in-part application of co-pending application Ser. No. 485,900, abandoned filed on Apr. 18, 1983 which is a continuation-in-part application of co-pending application Ser. No. 358,648, abandoned filed on Mar. 16, 1982.

BACKGROUND OF THE INVENTION

1. Field of the Invention

The present invention relates generally to ventilators for supporting ventilation in air breathing animals. More particularly, the present invention relates to high frequency ventilators which operate by oscillating respiratory air supplied to a subject at a frequency above the normal breathing frequency of the subject.

2. Discussion of Related Art

The use of a medical apparatus to facilitate breathing in mammals is well known in the art. The apparatus may take the form of a simple oxygen mask or tent which supplies oxygen at slightly above atmospheric pressure. Such devices merely assist a person to breather and work with the person's lungs.

Ventilators which operate at high frequency have been suggested in the past. There are two types of high frequency ventilators known in the art. One type, as exemplified by U.S. Pat. No. 2,918,917 to Emerson, employs a reciprocating diaphragm to vibrate a column of gas supplied to a subject. The vibration is in addition to the subject's respiration, natural or artificial, and at a much more rapid rate, for example, from 100 to more than 1500 vibrations per minute. The Emerson apparatus is primarily designed to vibrate the patient's airway and organs associated therewith, although Emerson also recognized that high frequency vibration causes the gas to diffuse more rapidly within the airway and therefore aids the breathing function. However, the Emerson apparatus is capable of supporting the patient's full ventilation and must be used in conjunction with the patient's spontaneous breathing or with another apparatus which produces artificially induced inhalation and exhalation.

The second type of high frequency ventilator is the jet pulse ventilator as exemplified in Schwanbom et al. U.S. Pat. No. 4,265,237. The Schwanbom et al ventilator produces high frequency, high pressure pulses of air which are capable of fully ventilating a patient. The respiration pulse enters with a pressure of 0.2 bar (209 cmH$_2$O) to 2.7 bar (2797.2 cmH$_2$O). This pressure is sufficient to expand the lungs during inspiration. Expiration is caused by the natural compliance of the lungs after the jet of air is stopped. Accordingly, it can be seen that Schwanbom et al must rely on the compliance of the lungs in order to fully ventilate the patient. If the lung compliance is low, greater pressure must be used. Schwanbom et al also supply a source of lower pressure gas for spontaneous breathing by the patient. While such jet pulse ventilators are useful for some applications, they are not generally applicable and their use is limited mostly to experimental work.

U.S. Pat. No. 4,155,356 to Venegas discloses a respiration assisting apparatus using high frequency pulses to hold a patient's airway open while the patient is breathing or being ventilated with a volume respirator. As with the Emerson device, Venegas is not capable of fully ventilating a subject and must rely either on the natural respiration cycle or on a volume type respirator to sustain the subject.

It is believed that normal breathing functions of air breathing animals are caused by expansion of the chest cavity. The expansion puts a negative pressure on the outside of the plurality of alveolar sacs in the lungs. The innumerable alveolar sacs receive air from the tidal flow or air movements generated, replenishing the sacs with oxygen containing gas and removing carbon dioxide containing gas. Normal breathing produces slight pressure differentials on the alveolar sacs to provide the breathing function. The compliance of the sacs causes them to inflate and deflate in response to the pressure changes.

When the chest cavity expands and creates a negative pressure on the outside of the alveolar sacs, it is believed this causes the sacs to inflate and provides movement of air into the alveolar sacs due to the pressure change. In order to exhale, the pressure on the outside of the alveolar sacs is increased by relaxing the chest cavity, causing the elastic alveolar sacs to collapse and allowing expiration.

As far as is known, commercially available prior art ventilators use a high positive air pressure to inflate the lungs like a balloon. If too much pressure is utilized, the compliance or elasticity of the alveolar sacs is reduced. Eventually, the damage will become so extensive that the sacs will no longer function to expel gas and thereby provide oxygen and carbon dioxide exchange.

When a person is hooked up to ventilator monitoring of blood gases is used to determine whether or not sufficient oxygen exchange is occurring in the alveolar sacs. When the blood gases deteriorate, present ventilators must correct the problem by increasing the pressure of the gas flowing into the lungs. The increase in pressure affects the compliance and elasticity of the sacs even more and can eventually destroy the lungs. A person essentially become addicted to a ventilator and must gradually be weaned from the ventilator.

When there is no lung disease one can use a low pressure with a respirator, because the lungs can breathe on their own to provide the exchange of gases in the alveolar sacs. When there is lung disease present, it may not be possible for the lungs to provide adequate ventilation or gas exchange in the alveolar sacs. This requires some means of facilitating the gas exchange.

The failure of ventilation in conventionally available ventilators generally begins with expiration failures. As mentioned earlier, the conventional method for increasing gas exchange when blood gases deteriorate is to increase the presence of the gas flowing into the lungs. The lungs can sustain a slight over pressuring for a short period of time and not incur permanent damage. However, continued over pressuring will cause a change in the compliance of the alveolar sacs. A bleb or rupture can occur when the alveolar sac has exceeded its elastic limit. Hemorrhaging may result, which destroys the ability of the sac to effect gas exchange and may cause other complications.

During normal breathing, it is believed that the alveolar sacs gradually deflate until they are no longer providing adequate gas exchange. In order to reinflate the alveolar sacs, an individual must sigh, reinflating the alveolar sacs to their full size. Failure to periodically sigh can be fatal because normal breaths allow the alveolar sacs to slowly deflate.

SUMMARY OF THE INVENTION

An object of the present invention is to provide a ventilator which will produce sufficient gas exchange to sustain full ventilation of a patient without overpressurizing the patient's lungs.

Another object of the present invention is to provide a ventilator which does not change the compliance of the alveolar sacs.

A further object of the present invention is to provide a sufficient volume of air exchange, combined with enhanced molecular diffusion of the gases, in the lungs to support full ventilation.

A still further object of the present invention is to provide mucocilliary clearance to remove fluid and mucous from the lungs.

Yet another object of the present invention is to allow the patient to sigh periodically and fully reinflate the alveolar sacs.

In accordance with the above and other objects, the present invention is an apparatus for supporting full ventilation of an air breathing animal, comprising a source of gas for respirating the animal and means for supplying a continuous flow of the gas from the source at a flow rate. A means for generating a high frequency pressure wave in said continuous flow of gas is provided and the flow of gas with the high frequency wave is connected to the lungs of an animal to be ventilated.

In accordance with other aspects, the invention includes means for maintaining an elevated static airway pressure in the animal, and the generating means comprises a linear motor.

The generating means further comprises means for driving the linear motor with a square wave signal.

Also in accordance with the above objects, the invention is an apparatus for supporting full ventilation in an air breathing animal, comprising a source of respirating gas, means for supplying the respirating gas to an airway of an animal, and means for producing a high frequency pressure wave in the gas, the wave having a positive sloped portion forcing gas into the airway and a negative sloped portion drawing gas out of the airway.

The pressure wave is polarized relative to the static airway pressure in the airway such that the pressure wave has positive and negative amplitude portions relative to the static airway pressure.

The invention may also include means for independently varying the duration of the positive portion of the pressure wave and the negative portion of the pressure wave to vary the inspiration to expiration ratio of the subject.

Also in accordance with the above objects, the invention includes a method for ventilating an air breathing animal, comprising producing a continuous flow of ventilating gas, supplying said continuous flow of gas to an animal to be ventilated, generating a high frequency pressure wave in said flowing gas, said pressure wave being generated with positively and negatively sloped portions to actively force gas into and draw gas out of said animal, and venting gas at a rate equal to the rate of flow of said gas, whereby carbon dioxide from said animal and ventilating gas are exchanged and diffused throughout the airway of said animal and said flowing gas in such a manner that sufficient ventilating gas reaches the alveolar sacs of said animal to support full ventilation without spontaneous breathing by said animal or the use of additional ventilating devices, and said vented gas removed carbon dioxide from the animal.

DESCRIPTION OF THE PREFERRED EMBODIMENTS

The preferred embodiment of the invention is a ventilator which uses a signal generator which produces a variable frequency, variable period square wave signal. The signal is directed through an amplifier which has a variable power output. A polar converter converts the square wave to a polar square wave. The amplifier drives a bidirectional linear motor which is connected to a diaphragm which supplied energy to gas in the ventilator. Due to the bidirectional motor, the pressure wave produced has a first portion with a positive slope and a second portion with a negative slope. This causes respirating gas to be both moved into the subject's airway and withdrawn from the subject's airway. Due to the fact that the square wave is polar, the diaphragm produces a positive and negative pressure in each cycle, relative to the static airway pressure of the subject.

Figure 1:
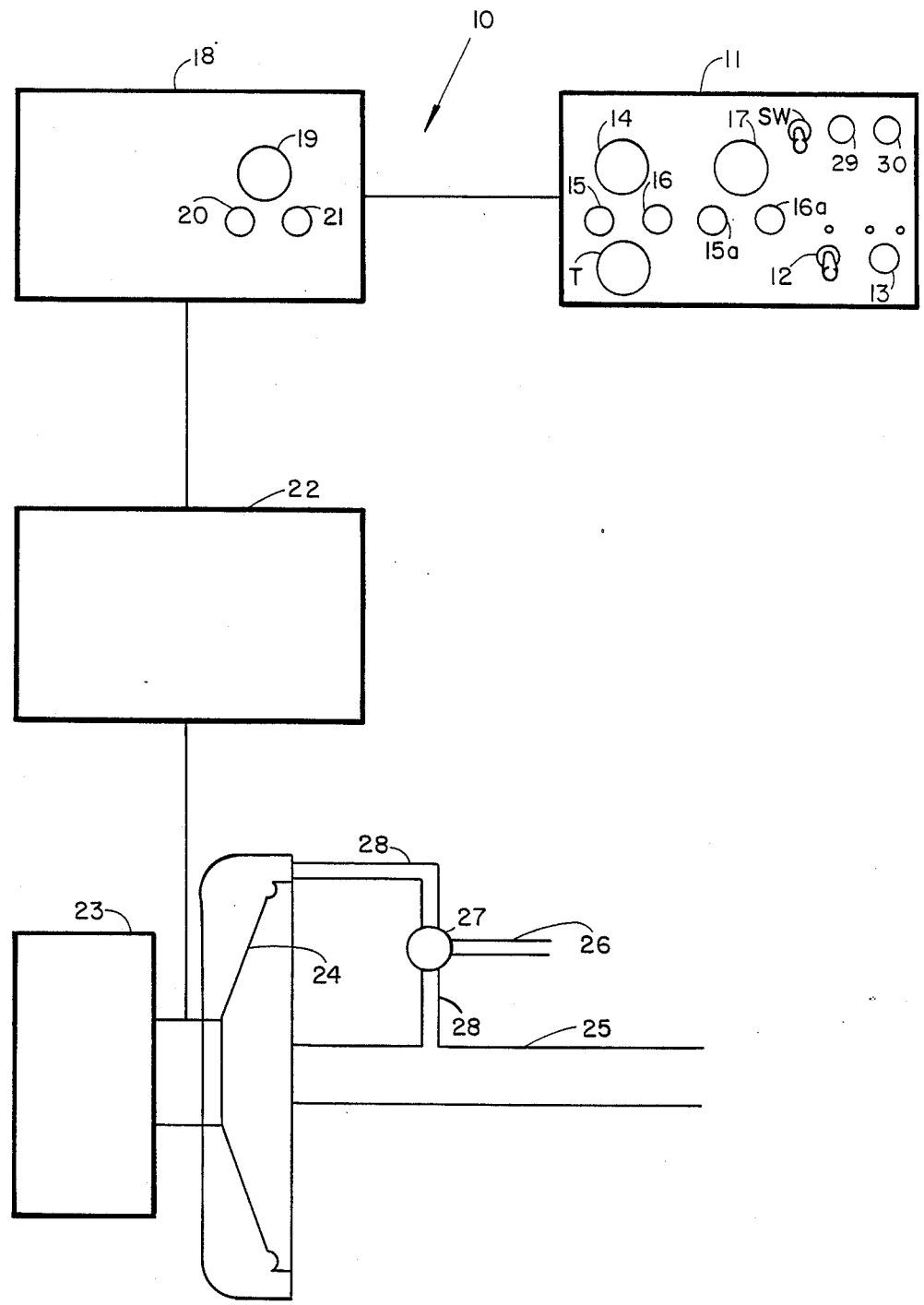
FIG. 1 is a block diagram of a first embodiment of a high frequency ventilator according to the present invention.

Referring to FIG. 1 of the drawing, there is shown a schematic view of a high frequency ventilator 10 according to the present invention. The high frequency ventilator 10 includes a signal generator 11. When the toggle switch 12 is turned on, an hour meter T begins running and the signal generator begins operation. Control knob 13 selects one of the two channels which may be alternately selected. A meter 14 indicates the frequency of the signal generated for the selected channel. The control knobs 15 and 16 set the frequency for the first and second channels respectively. The control knobs 15a and 16a control the I:E ratio for the respective first and second channels. A meter 17 indicates the period of the square wave signal generated, which coincides with the inspiration to expiration ratio or the I:E ratio. The apparatus is capable of varying the I:E ratio from about 80:20 to 20:80, a range useful in achieving desired waveforms during clinical applications of the machine. The I:E ratio is the duration of the inspiration or positive period of the cycle over the expiration or negative period of the cycle.

A sigh function is provided by a sigh timer which is controlled by switch SW and control knobs 29 and 30. When the switch SW is on and the control knob 13 is set on channel one, the setting of knob 29 provides a predetermined first period of time to elapse during which the system operates on channel one. At the end of the first predetermined period of time, the sigh timer causes the machine to change to nchannel two for a second predetermined period of time as set by control knob 30. The sigh function is set on channel two by adjusting the frequency, I:E ratio and power with knobs 16, 16a and 21 respectively. The sigh function provides a breath of gas of sufficient volume and duration to enable the alveolar sacs of the patient to reinflate. Channel two may be set to a frequency of about ½ hz for the sigh and is set at a high power. This produces a high power, low duration output which operates essentially in the manner of a volume ventilator. After the second predetermined period of time has elapsed, the machine reverts to operation on channel one for the first predetermined period of time. The machine continues cycling between channels one and two when switch SW is in the on position.

The signal produced by the signal generator is a variable frequency, variable period square wave. This signal is directed to an amplifier 18 which is connected to the signal generator. High frequency ventilation is considered to begin at about 3 Hz and extends above this value. The output of the amplifier 18 is shown on the meter 19 and the power gain is adjusted by control knobs 20 and 21 which control the first and second channels, respectively. The signal generated by the amplifier is a variable power, variable frequency and variable period square wave.

The signal from the amplifier 18 passes to a polar converter 22 which is connected with the amplifier. The polar converter 22 serves the dual function of polarizing the square wave and providing a connection between the power supply and a linear motor 23. Linear motor 23 includes a diaphragm 24 which converts mechanical motion to pressure waves in gas. Diaphragm 24 transmits energy to gas in a respirator line 25. Oxygen or compressed gas is added to the system through line 26, a manual two-way needle vale 27 and line 28 to maintain a positive low static pressure on the order of 1 to 15 centimeters of water for the non-diseased lung. A small orifice may be substituted for the valve 27 for economy. For diseased lungs the positive low pressure may be on the order of 7 to 40 centimeters of water. The above pressures have been empirically demonstrated. The valve 27 allows pressure on both sides of the diaphragm to equalize to the mean airway pressure in line 25. A change in mean airway pressure is believed to not affect the waveform because of the equalization. The mean airway pressure (MAP) is the average pressure in the airways of an air breathing animal. Line 25 is connected to an endotracheal tube to supply gas to the patient. A gas exit from line 25 is connected to a line from which gas leaves the system. Appropriate valves and filters are provided as will be discussed hereinafter.

In operation, channel 1 of the signal generator 11 is set to produce a frequency of 3 Hz or greater and channel 2 is set to produce a lower frequency suitable for producing a sigh function. A frequency on the order of about 30 cycles per minute is satisfactory for the sigh function. The desired I:E ratio is set and a source of pressurized gas is attached to line 26. Valve 27 is set such that a flow rate of approximately 5 liters per minute is achieved. The valves in line 30 are set so that the static pressure in tube 29 is relatively low yet sufficient to hold the lungs of the subject open. A static pressure of about 10 cm of water, for example, has been found to be satisfactory for this purpose in a non-diseased lung. The system is operated in this condition to fully respirate the subject.

During the operation of channel 1, respirating gas is supplied at a rate of 5 liters per minute into line 25 and gases from line 25 exit into outlet line 30 at the same rate. However, because the concentration of pure respirating gas in line 25 is greater than the concentration of gas contaminated with carbon dioxide from the subject in tube 29 the pure respirating gas is diffused through tube 29 into the subject's lungs. The diffusion acts with a volume exchange effect produced by the bidirectional drive of motor 23 to cause gas exchange in the lungs. Although the mechanism for causing complete gas exchange is not completely understood, it is believed to be a combination of molecular diffusion, asympathetic vibrations of the lung tissue and volume exchange.

It is believed that molecular diffusion is greatly responsible for the gas exchange. This diffusion is enhanced by the vibrational energy added through diaphragm 24 to the point where much of the respirating gas reaches the subject's lungs and replaces the carbon dioxide therein. This gas exchange can be more clearly envisioned by viewing the source of gas from line 26, as supplying, for example, oxygenated air which produces an oxygen gradient throughout tube 29 with a higher partial pressure of oxygen existing at the outlet of line 28 than in the rest of the system. The subject's lungs can be viewed as a source of carbon dioxide which produces a $CO_2$ gradient throughout tube 29. The partial pressure of the $CO_2$ is greater in the lungs than in the rest of the system. What the ventilator of the present invention does is to promote the diffusion of these gases throughout the tube 29, lines 25 and lungs of the subject to such an extent that a large portion of the oxygen reaches the alveolar sacs of the patient. It should also be understood that the static pressure produced by valves 30 is also present to hold the air passages open thereby ensuring that diffusion can take place. This is to be clearly contrasted with the presently known volume ventilators which use high pressure gas to actually inflate the subject's lungs to produce only a volume exchange whereby oxygenated gas is forced under pressure into the lungs to expand the lungs during inspiration and the compliance of the lungs forces the carbon dioxide out during expiration. These known ventilators produce a volume exchange of gas analogous to the normal breathing function.

The asympathetic vibrations of the subject's lungs appear to promote mixing of the gases deep in the lungs and therefore also enhance gas exchange. These vibrations also appear to aid in moving gases into and out of the lungs.

The volume exchange effect caused by the present invention is due to the motor 23 which causes movement of diaphragm 24 in both directions thereby giving the resultant pressure wave positive and negative sloped portions. The positive sloped portion forces respirating gas into the subject's airway causing an instantaneous rise in pressure, while the negatively sloped portion actively draws gases out of the airway causing an instantaneous decrease in pressure. This type of gas exchange is to be contrasted with known high frequency jet ventilators which only force gas into the lungs and rely on the compliance of the lungs to push gas back out. In other words, jet ventilators produce pressure waves which only have a positive slope. If it were not for the natural phenomena occuring apart from the jet ventilator, the pressure in the subject's lungs could rise indefinitely, whereas the present invention forces the pressure in the lungs to return to a lower level by actively drawing gases back out.

As discussed above, the signal driving motor 23 is a polar square wave. Ideally, the pressure wave produced in line 25 should also be square in shape. However, this pressure wave would not have a perfect square shape as it emerges from the end of tube 29 in the subject's lungs. The deviation of shape is due to the fluid flow characteristics of the line 25 and tube 29 and compressibility of the gases. In actuality, electrical and pressure waveforms are not perfect in shape. Accordingly, applicant's waveforms, which are characterized as square waves, exhibit for each cycle a relatively rapid rise, a relatively horizontal portion, a relatively rapid decline and a relatively horizontal portion. This is distinguished from high frequency sine waves oscillatory ventilators such as the Emerson patent which constitute part of the prior art. Such sine wave oscillators have been used experimentally but have not been commercially developed as far as known. High frequency jet ventilators exhibit a sawtooth pressure wave, namely a relatively rapid rise, a relatively gradual decline to a value greater than static airway pressure.

Also as discussed above, the amplitude of the pressure wave can be varied to suit different needs. In accordance with the desirable features of maintaining a low pressure in the lungs of the subject, the pressure wave is polar; that is, has both a positive portion and a negative portion relative to the static airway pressure in the patient. In this manner, the pulse amplitude does not affect the mean airway pressure except to the extent produced by a difference in pulse width of the positive and negative portions of the pulses. Thus, the mean airway pressure is held at approximately the static pressure set by the valves in line 30. Each electrical pulse and hence each pressure pulse has a positive going portion and a negative going portion. Due to the connection of line 28 of FIG. 1, the positive and negative going portions of the pressure pulse are relative to the static airway pressure and thus the static airway pressure is equal to the mean airway pressure.

As long as these positive and negative going portions are kept within reasonable limits, there is no danger of overpressurizing the lungs of the subject. It has been found that a peak to peak amplitude can be used as a greater static airway pressure is used. For severely damages lungs, it may be necessary to use a static pressure as high as 40 cm $H_2O$. Care should be taken to be sure that the instantaneous pressure caused by the system in the lungs does not reach a level low enough to cause lung collapse.

The pressure wave may vary between 5 cm $H_2O$ and 15 cm $H_2O$. That is, on the forward stroke of motor 40, the pressure in the subject's lungs is raised by 10 cm $H_2O$ by forcing gas into the lungs. On the rearward stroke of motor 40, the pressure wave is forced to fall from 15 cm $H_2O$ to 5 cm $H_2O$ thereby drawing gas out of the lungs. At the same time, the pressure wave is polar relative to the 10 cm $H_2O$ static pressure level produced by setting the values in line 30. Thus, the mean airway pressure is maintained at approximately 10 cm $H_2O$. The peak to peak amplitude (power) of the pressure wave can be varied without affecting the subject's means airway pressure. Likewise, the subject's mean airway pressure can be set independently of the pressure wave amplitude by adjusting the static pressure of the ventilation to the desired mean pressure value.

As should be clear from the foregoing example, the flow of gas into line 26 should be maintained at a constant rate since this flow provides the source of fresh respirating gas and also acts with the valves in line 30 to maintain the static pressure.

Channel two of the ventilator is set to have a much lower frequency and a much higher positive amplitude. When the control switches to channel two, the low frequency, high amplitude movement of the diaphragm 24 creates a volume displacement of air into the patient's lungs to produce a sigh effect. The characteristics of a volume movement sufficient to produce a proper sigh effect are well known in the art and shall not be discussed in detail. It should be understood, however, that the sigh function is independent of the high frequency ventilation function.

The second channel is also useful for providing a second high frequency signal which can be alternated with the first high frequency signal. Different high frequencies may be beneficial to produce different results. For example, one frequency may be found to be beneficial for the removal of mucous while a second frequency may produce more efficient air exchange. Accordingly, by providing the ventilator with the ability to automatically switch between two such frequencies both desired results could be achieved most efficiently.

The electrical circuitry of the ventilator will now be discussed in detail with reference to FIG. 11, which shows the ventilator with only one signal generating channel for simplicity.

Figure 11:
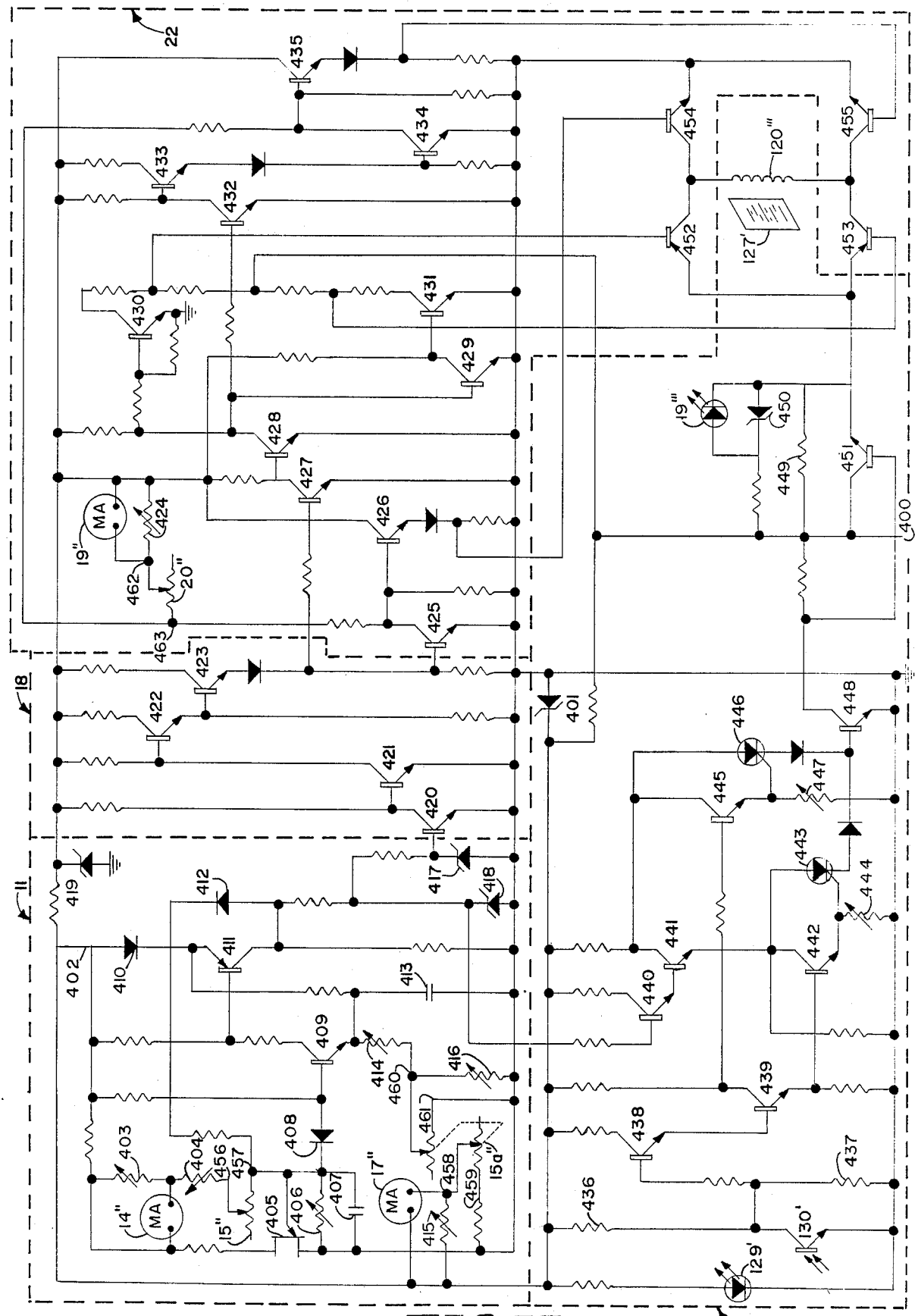
FIG. 11 is a schematic circuit diagram showing the electrical circuit used in the embodiments of FIGS. 1 and 3.

In FIG. 11, a positive DC voltage is shown applied to the circuit at point 400. A zener diode and resistor at point 401 reduce the voltage to 15V. The signal generator section begins at point 402. Milliammeter 14" measures the current flowing to the emitter of unijunction transistor 405. Variable resistor 403 is adjusted to cause milliammeter 14" to indicate the frequency of the signal. Variable resistor 404 is adjusted to limit the maximum frequency of the circuit. Potentiometer 15" allows the operator to select any frequency between the minimum and the maximum. Variable resistor 406 is adjusted to bleed the emitter leakage current of unijunction transistor 405 which prevents capacitor 407 from being charged except through potentiometer 15".

As capacitor 407 is charged, the voltage at the emitter of unijunction transistor 405 rises until it reaches a fixed proportion of the differential between base 1 and base 2 of the unijunction transistor 405 at which time it conducts which discharges capacitor 407 and causes diodes 408 to become forward biased. The signal at the cathode of diode 408 is a sawtooth wave typical of an astable unijunction relaxation oscillator and its frequency is variable through potentiometer 15″.

As diode 408 becomes forward biased due to the negative resistance effect of unijunction transistor 405, it causes transistor 409 to turn off which in turn causes transistor 411 to turn off. As the base of transistor 409 becomes positive again, it begins to conduct and transistor 411 turns on after a period of time determined by potentiometer 15a″. Capacitor 413 drives transistor 411 into saturation and it remains on until unijunction transistor 405 again conducts which provides the positive portion of the square wave. Diodes 410 and 412 add to the stability of the circuit by providing a base bias voltage differential to transistor 411 and feedback to the emitter of unijunction transistor 405. Variable resistors 414, 415 and 416 with milliammeter 17″ and potentiometer 15a″ comprise the means whereby the square wave signal is made a variable period square wave and of indicating its condition of variability as percent inspiration on milliammeter 17″. When the resistance of potentiometer 15a″ is at the minimum, the current through milliammeter 17″ is at the maximum indicating a high inspiration percent and the charging time of capacitor 413 is at the maximum. Variable resistor 415 is a shunt for milliammeter 17″ which allows it to be calibrated to indicate the exact percent of inspiration of the invention. Variable resistor 414 sets the maximum inspiration percentage and variable resistor 416 allows calibration of potentiometer 15a″.

Zener diodes 417 and 418 condition the variable frequency variable period square wave to one of constant amplitude. Without them, the positive amplitude of the square wave varied with the duty cycle. The zener diode and resistor at points 419 reduce the voltage to the amplifier section to 5V. Transistor 420, 421, 422 and 423 comprise a means whereby the low power signal at the base of transistor 420 is amplified.

Transistors 452, 453, 453 and 455 comprise the driving transistors of the polar converter which apply a bipolar signal to coil 120‴ of the linear motor which produces the pressure variations in the gas in the ventilator. When transistors 452 and 455 are on while transistors 453 and 454 are off, current flows through coil 120‴ in one direction. Transistors 452 and 453 are used in a switching mode and are either biased off or driven into saturation. Transistors 454 and 455 are used in the transient regions and are biased off but the extent to which they are turned on is determined by potentiometer 20″.

When transistor 423 is on, transistor 425 is on and transistor 426 is off thereby biasing transistor 454 off. Transistor 427 is on, transistor 428 is off, transistor 429 is on and transistor 431 is off thereby biasing transistor 453 off. Simultaneously, transistor 430 is on, transistor 433 is off, transistor 434 is off and transistor 435 is biased on to the degree allowed by the current flowing through potentiometer 20″. Transistor 455 is thereby biased on relative to the position of potentiometer 20″.

When transistor 423 is off, transistor 425 is off and transistor 426 is biased on to the degree allowed by potentiometer 20″ and consequently transistor 454 is biased on proportionally to the setting of potentiometer 20″. Transistor 427 is off, transistor 428 is on, transistor 429 is off and transistor 431 is on thereby biasing transistor 453 on. Simultaneously, transistor 430 is off which biases transistor 452 off. Transistor 432 is off, transistor 433 is on, transistor 434 is on and transistor 435 is off which biases transistor 455 off.

Milliammeter 19″ indicates the relative percent of power applied to coil 120‴ and is calibrated by variable resistor 424.

The remaining circuitry of FIG. 11 is to prevent mechanical contact between moving and stationary masses. A mirror 127' is mounted so that it moves with the coil 120‴. An infrared light emitting diode 129' is directed at the mirror 127'. Mounted next to the diode 129' is an infrared transistor 130'. As the line of sight distance changes between diode 129' and transistor 130' due to the movement of the mirror 127', the voltage at the base of transistor 438 varies. Resistors 436 and 437 provide a voltage divider with an effective variable resistance through transistor 130'. Transistor 438 amplifies and inverts the signal at the collector of transistor 130'. Transistor 440 is driven by the square wave signal present at the anode of zener diode 418 which is amplified by transistor 441. Therefore, at the anode of silicon controlled rectifier 443, there is an opposite signal to that at the anode of silicon controlled rectifier 446.

As the current at the base of transistor 438 increases, so does the current at the base of transistor 439. As transistor 439 conducts more, transistor 445 tends to conduct less. Simultaneously, transistor 442 tends to conduct more. Variable resistor 444 determines the current through the emitter of transistor 442 necessary to turn on silicon controlled rectifier 443. The polarity of the coil 120‴ is maintained in phase with the signal at zener diode 418 to cause the anode of SCR 443 to be positive when the current at the base of transistor 438 is increasing due to the movement of coil 120‴. When SCR 443 is turned on, it turns on transistor 448 which turns off transistor 451 which reduces the amount of current available to coil 120‴ by shunting it through resistor 449 thereby limiting the travel of coil 120‴. When the signal at zener diode 418 reverses, the voltage at the anode of SCR 443 falls below its minimum conduction limits which turns it off and consequently transistor 448 goes off and transistor 451 turns back on allowing full power to the coil 120‴. When transistor 451 is off, light emitting diode 19‴ is on and it is protected by zener diode 450.

As the current at the base of transistor 438 decreases, transistor 438 tends to conduct less causing a greater current at the base of transistor 445. Variable resistor 447 controls the point at which SCR 446 turns on. Being in phase, as transistor 445 turns on, the voltage at the anode of SCR 446 is positive and its operation is similar to SCR 443.

Figure 12:
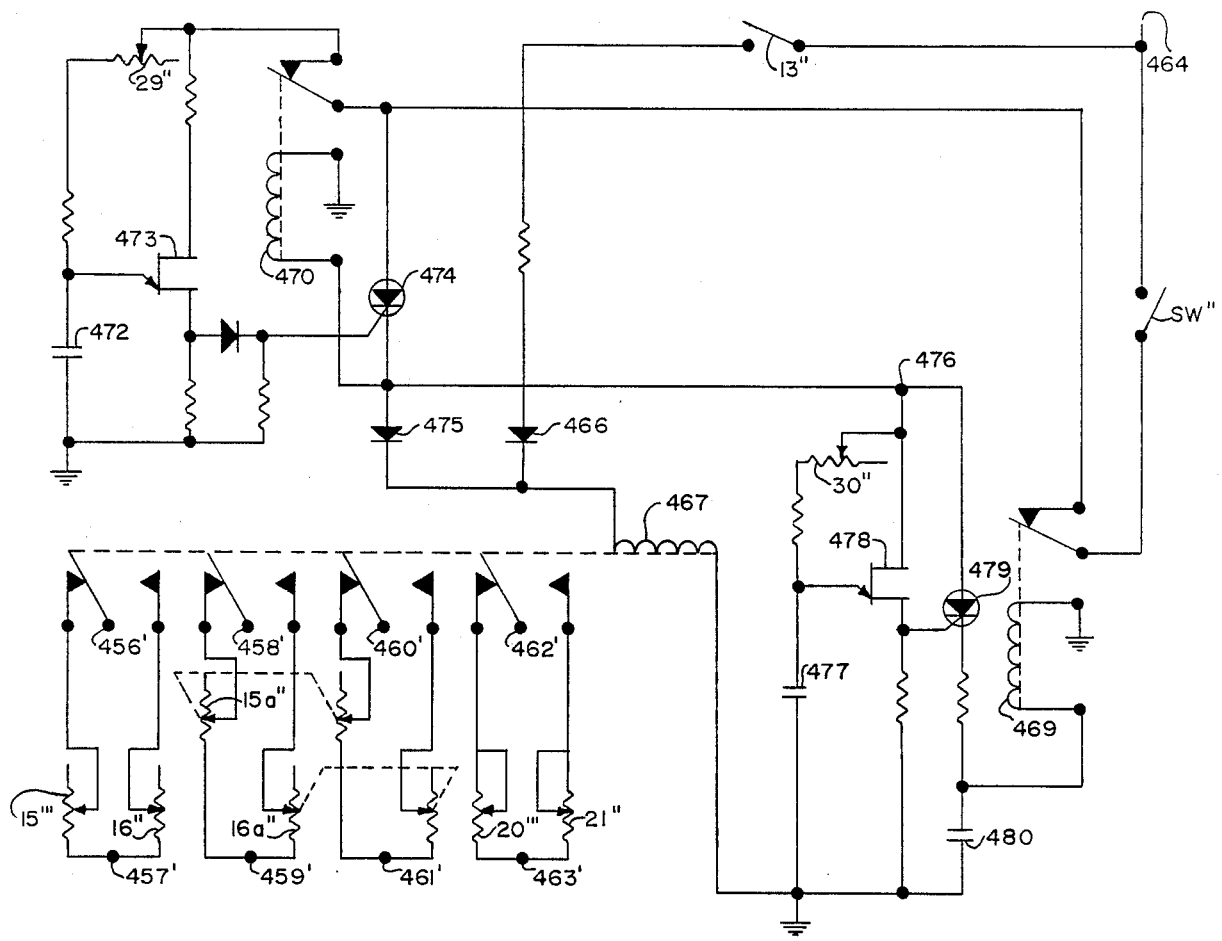
FIG. 12 is a schematic circuit for providing two independent sets of operating parameters for producing a two channel output.

FIG. 12 is an electronic schematic diagram showing a timer for use in circuit 11 which produces two independent operating channels for the present invention and automatically switches back and forth between them. In FIG. 12, a DC voltage is applied at point 464. For the purposes of this disclosure, the circuit represented in FIG. 11 is changed by removing potentiometer 15″ and connecting points 456 and 457 to points 456' and 457' respectively, of FIG. 12. Additionally, potentiometers 15a″ and 20″ as shown in FIG. 11 are removed and points 458, 459, 460, 461, 462 and 463 are connected to points 458′, 459′, 460′, 461′, 462′ and 463′ respectively of FIG. 12.

When switch 13″ is open, relay 467's contact remain in their normally closed position. Potentiometer 15‴ therefore controls frequency, potentiometer 15a″ controls the period of inspiration or duty cycle and indication of it; and potentiometer 20‴ controls the power. When switch 13″ is closed, relay 467 is energized which causes potentiometers 15‴, 16a″ and 21″ to control frequency percent inspiration and power respectively, thereby giving a second set of independent operating parameters. Operationally, when switch 13″ is open, the machine is said to be operating on "channel one". When switch 13″ is closed, the machine is said to be operating on "channel two".

Automatic switching between channels one and two is accomplished by leaving switch 13″ open and closing switch SW‴. Current then flows through the normally closed contacts of relays 469 and 470. Potentiometer 29″ controls the time that capacitor 472 takes to charge. When the emitter voltage of unijunction transistor 473 reaches a fixed porportion of the voltage between its base 1 and base 2 leads, it will conduct sending a pulse to the gate of SCR 474 which turns it on. Relay 470 is energized which interrupts current to this "CHANNEL 1 DURATION" circuit. Relay 467 is also energized which causes switching to channel 2 as described above. This first preset period of time set by potentiometer 29″ is adjustable by the operator.

Current is also now applied to the "CHANNEL 2 DURATION" circuit beginning at point 476. Potentiometer 30″ controls the time that capacitor 477 takes to charge. When the emitter voltage of unijunction transistor 478 reaches a fixed proportion of the voltage between its base 1 and base 2 leads, it will conduct sending a pulse to the gate of SCR 479 which turns it on which in turn charges capacitor 480 and energizes relay 469 which interrupts the current to SCR 474 which in turn de-energizes relays 369, 470 and 467 which resets the entire circuit. This second preset period of time set by potentiometer 30″ is adjustable by the operator. The machine will continue to switch back and forth between channel 1 and channel 2 until SW‴ is opened or switch 13″ is closed. Diodes 475 and 466 isolate the circuit functions.

Figure 5:
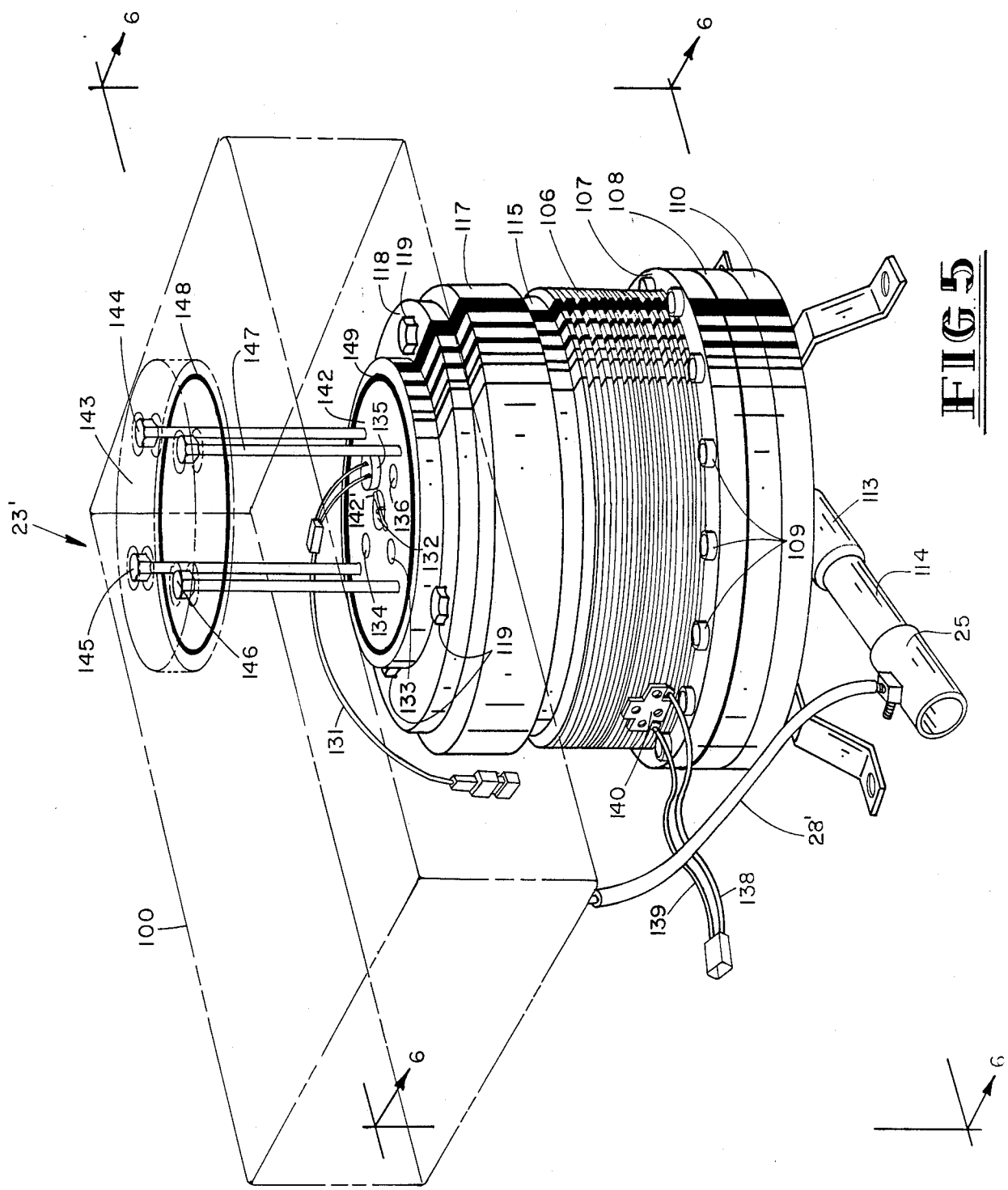
FIG. 5 is a perspective view of a linear motor used in the present invention.
Figure 6:
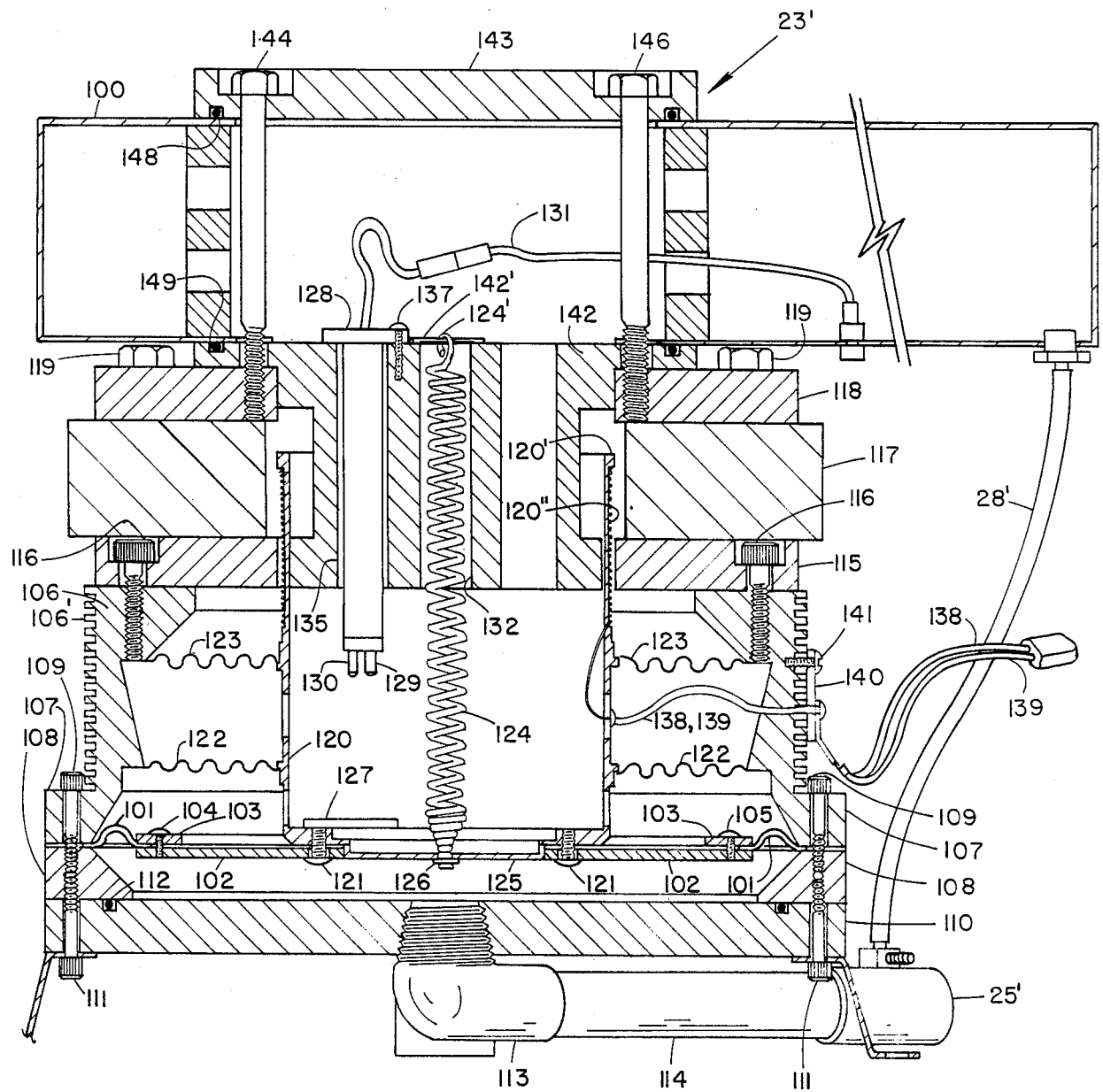
FIG. 6 is an elevational sectional view of the linear motor taken along line 6—6 of FIG. 5.

Referring to FIGS. 5 and 6 there is shown a linear motor 23′ for use in a ventilator according to any of the embodiments of the present invention. The linear motor 23′ includes a pressure chamber 100 at the upper end thereof. The pressure chamber 100 is connected with one side of a diaphragm 101 and piston member 102. The diaphragm 101 is connected to piston member 102 by retaining ring piston flange 103 through a plurality of screws, 104 and 105 being shown.

Linear motor 23′ includes a housing member 106 having cooling fins 106′ and a flange 107. The flange 107 is connected to flange 108 by a plurality of screws 109. The diaphragm 101 is clamped between the flanges 107 and 108 and as shown in FIG. 6 includes a raised portion to allow for its movement.

The flange 108 is connected to an outlet plate 110 by a plurality of screws 111 opposed to screws 109. O-ring 112 provides a seal between the flange 108 and the outlet plate 110. The diaphragm 101 is made of flexible rubber material and provides a seal between the flange 107 and flange 108. An L-shaped coupling 113 is connected to the outlet plate 110 and is in turn connected to the line 114 which is connected to the line 25′.

A top plate 115 is connected to the housing 106 by a plurality of screws 116. A magnet 117 is mounted between the top plate 115 and the back plate 118. A plurality of screws or bolts 119 connect the back plate 118 to the top plate 115 to clamp magnet 117 therebetween.

A coil form 120 is connected by a plurality of screws 121 to the piston member 102. The coil form 120 constitutes a moving mass.

Spiders or radial limiters 122 and 123 are glued to the housing 106 and the moving mass 120 and allow axial movement while preventing radial movement.

A tension spring 124 is connected to the end 125 of the cylindrical coil form 120 by connector means 126. A mirror 127 is mounted on the coil form end 125. A position sensor means 128 is provided with a LED light 129 and an infrared transistor 130. As the coil form 120 moves up and down so does the mirror 127 and the distance of the mirror 127 from the infrared transistor 130 is detected. This designates the position of the piston member 102 and diaphragm 101 at all times. a lead 131 is connected with the position sensor means 128 for conveying power thereto and a signal therefrom.

The tension spring 124 is connected at its upper end 124′ to the upper end of the pole piece 142 by connector pin 142′. The spring 124 extends through central bore 132 extending through the pole piece 142. A plurality of bores 133, 134, 135 and 136 also extend all the way through the pole piece 142. As shown in FIGS. 5 and 6, the position sensor means 128 extends through bore 135 and is connected thereto by screw means 137. The tension of spring 124 equals the weight of the moving mass of the coil form 120 and everything mounted thereon at the mid point which provides a weightless effect at that point. Electrical leads 138 and 139 connect to a terminal block 140 attached by screw 141. The terminal block 138 and 139 are then connected to the coil or winding 120″. As will be apparent the upper end 120′ of the coil form extends through the space between the pole piece 142 and the top plate 115 to allow up and down reciprocating motion of the coil form.

The pressure chamber 100 is connected to a cap means 143 by a plurality of screws 144, 145, 146 and 147 which are in turn connected to the back plate 118. O-rings 148 and 149 seal the pressure chamber 100 with the cap member 143 and the pole piece 142. The diaphragm 101, piston member 102 and coil member 120 covert mechanical motion to pressure waves in the gas. The larger the pressure chamber 100, the better, since the larger pressure chamber prevents substantial modulation of the pressure wave.

The current in the coil 120″ moves in two directions by reversing the current which causes the reciprocating motion of the linear motor.

Figure 2:
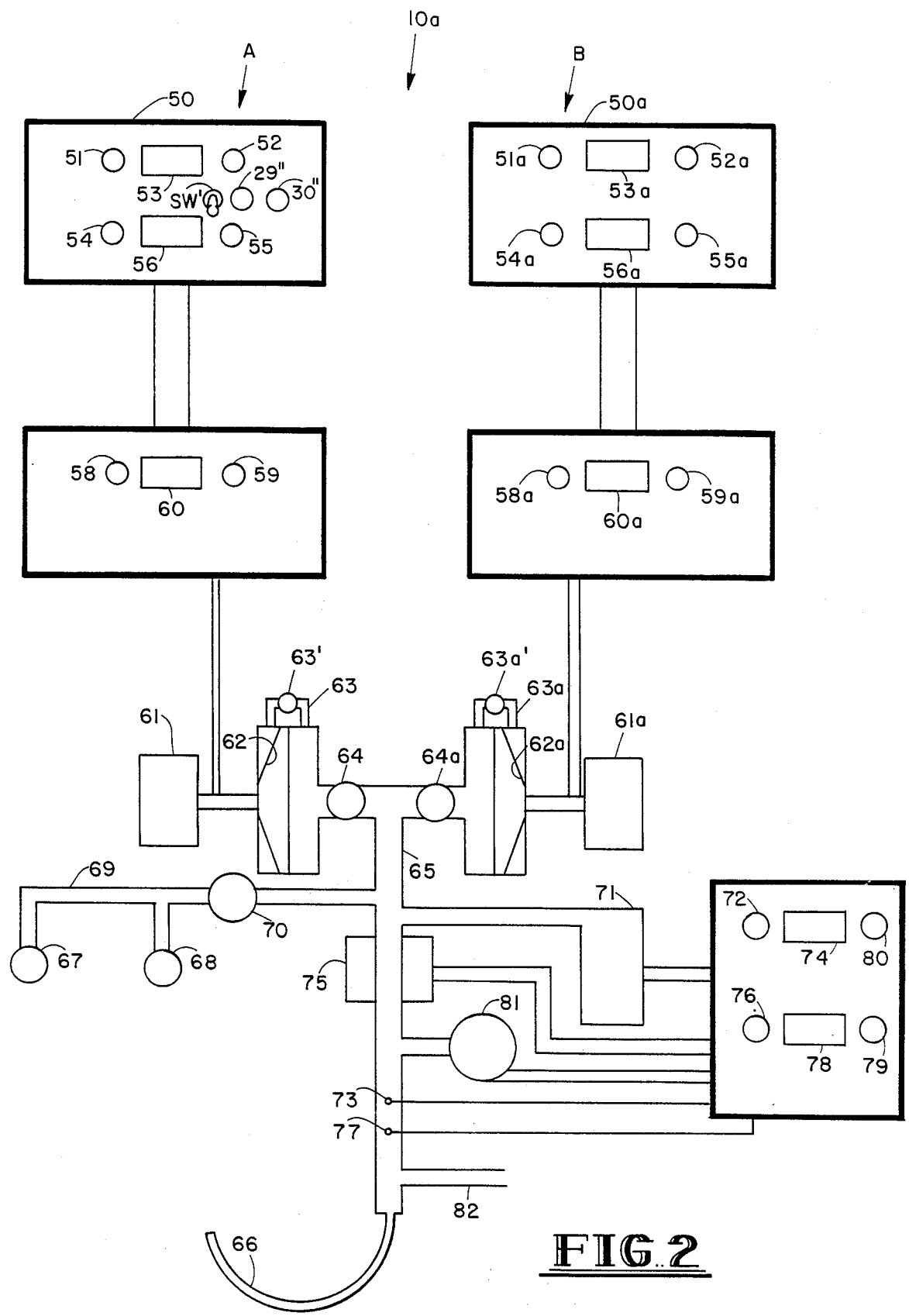
FIG. 2 is a block diagram of a second embodiment of a high frequency ventilator according to the present invention.

Another embodiment of the invention is shown in FIG. 2. The high frequency ventilator 10a in FIG. 2 includes a first system A and a second duplicate system B. A signal generator 50 produces a square wave which is frequency dependent on the setting of potentiometer control 51 for channel one or potentiometer control 52 for channel two. The frequency of the channel selected is displayed on digital meter 53. The period of each horizontal segment of the square wave generated is dependent upon the setting of control knobs 54 and 55 for the first and second channels, respectively, and the positive horizontal segment of the square waves is displayed on digital meter 56. The control knobs 54 and 55 allow the inspiration to expiration ratio (I:E) to be varied according to the needs of a patient.

The sigh function is provided by a sigh timer which is activated by switch SW' and control knobs 29" and 30". The operation is the same as the sigh timer for the ventilator 10 except for ventilator 10a it controls the switching between both the first and second channels of systems A and the third and fourth channels of system B.

The square wave signal from the first signal generator 50 is directed to amplifier 57 which provides a power gain according to the setting of control knobs 58 and 59 for the first and second channels, respectively. The percent of available power is displayed on digital meter 60. The first amplifier 57 also includes a polar converter which converts the square waves to polar square waves.

The polar square waves drive the linear motor 61 in both directions. As the diaphragm is driven back and forth, it creates a positive and negative pressure on the gas side of diaphragm 62. The movement of the diaphragm converts the energy of the electrical input to the linear motor to an energy wave in the gas.

At certain frequencies, the gas molecules are diffused into one another at the molecular level at greatly increased rates, as compared to the tidal flow associated with normal breathing. As discussed above, this phenomenon is apparently due to the energy added to the gas.

The apparatus also includes a second system B which has a signal generator 50a whose operation is identical to the first signal generator 50. The second signal generator 50a includes potentiometer controls 51a and 52a which control the frequency of channels three and four, respectively. The frequency is displayed on digital meter 53a. The period of the horizontal segment of the square waves for the third and fourth channels is dependent on the setting of control knobs 54a and 55a, respectively. Digital meter 56a displays the period of each positive horizontal segment of the square waves. As with the first signal generator 50, generator 50a allows the inspiration to expiration ratio (I:E) to be varied according to need.

The square wave signal from generator 50a is directed to a second amplifier 57a to provide a power gain for channels three and four, as controlled by the setting of control knobs 58a and 59a, respectively. The percent of available power is displayed on digital meter 60a. The second amplifier 57a includes a polar converter which converts the square waves from the signal generator 50a to polar square waves. Amplifier 57a is connected to a linear motor 61a which includes a diaphragm 62a.

Both sides of the diaphragm 62 are connected by a tubular connector 63 and valve 63'. Similarly, both sides of diaphragm 62a are connected by tubular connector 63a and valve 63a'. This provides an alternating positive and negative pressure to the ventilator line 65 and equalizes pressure on both sides of the diaphragm to mean airway pressure in ventilator line 65.

In operation, assuming the valve 64 is fully opened and the valve 64a is fully closed, the gas in the respiratory system, between the diaphragm 62 and the endotracheal tube 66 is being acted on by the diaphragm 62 as indicated on digital meters 53, 56 and 60. Compressed air at a pressure as disclosed for ventilator 10 is supplied through a valve 67 and oxygen is provided through valve 68 to the line 69 which is connected to a ventilator line 65. The setting of valves 67 and 68 determine the oxygen concentration of the gas. The rate of flow through the system is indicated by the flow meter 70 in line 69.

The humidity of the gas is increased by humidity generator 71 which is controlled by control knob 72. The humidity is sensed by a humidity sensor 73 and the humidity is indicated on digital meter 74.

The gas in the ventilator is heated by a heater 75 which is controlled by control knob 76. The temperature of the gas in the ventilator is sensed by the temperature sensor 77 and the temperature is displayed on the digital meter 78. An alarm is provided to go off when the temperature is not within certain limits as set by control knob 79. A control knob 80 sets an alarm for the humidity level. The mean airway pressure is indicated by the mean airway pressure gauge 81 which is equipped with a high and low alarm. Gas is discharged from the system through exhaust tube 82.

The signal generator 50 and amplifier 57 comprise a first signal generator means which along with the linear motor 61, diaphragm 62 and valve 64 comprise the first system A. The signal generator 50a and amplifier 57a comprise a second signal generator means which along with the linear motor 61a, diaphragm 62a and valve 64a comprise the second system B. Each system can be operated on two separate channels which are independently set. One channel may be set to certain parameters and then the operator is also able to return to the parameters of the other channel at any time.

As discussed above, a reason for having two channels per system is to provide a "sigh" function, which is a deep breath necessary to reinflate the alveolar sacs, several times per hour. An advantage of having two redundant systems is to provide reliability during critical applications. Another advantage of the dual system is that a high frequency wave can be superimposed on a low frequency wave. This will facilitate mucoilliary clearance which is known to be enhanced by a single high frequency wave. Actually, the main benefit derived by a high frequency wave on a low frequency is to introduce physicians to the benefits of high frequency ventilation slowly. The low frequency wave can be operated as a conventional volume ventilator if the physician is not familiar with total high frequency ventilation. After the merits of high frequency ventilation become more generally accepted, the use of the low frequency can be discontinued. The valves 64 and 64a allow any combination of superimposed waves within the limits of the individual systems.

Figure 3:
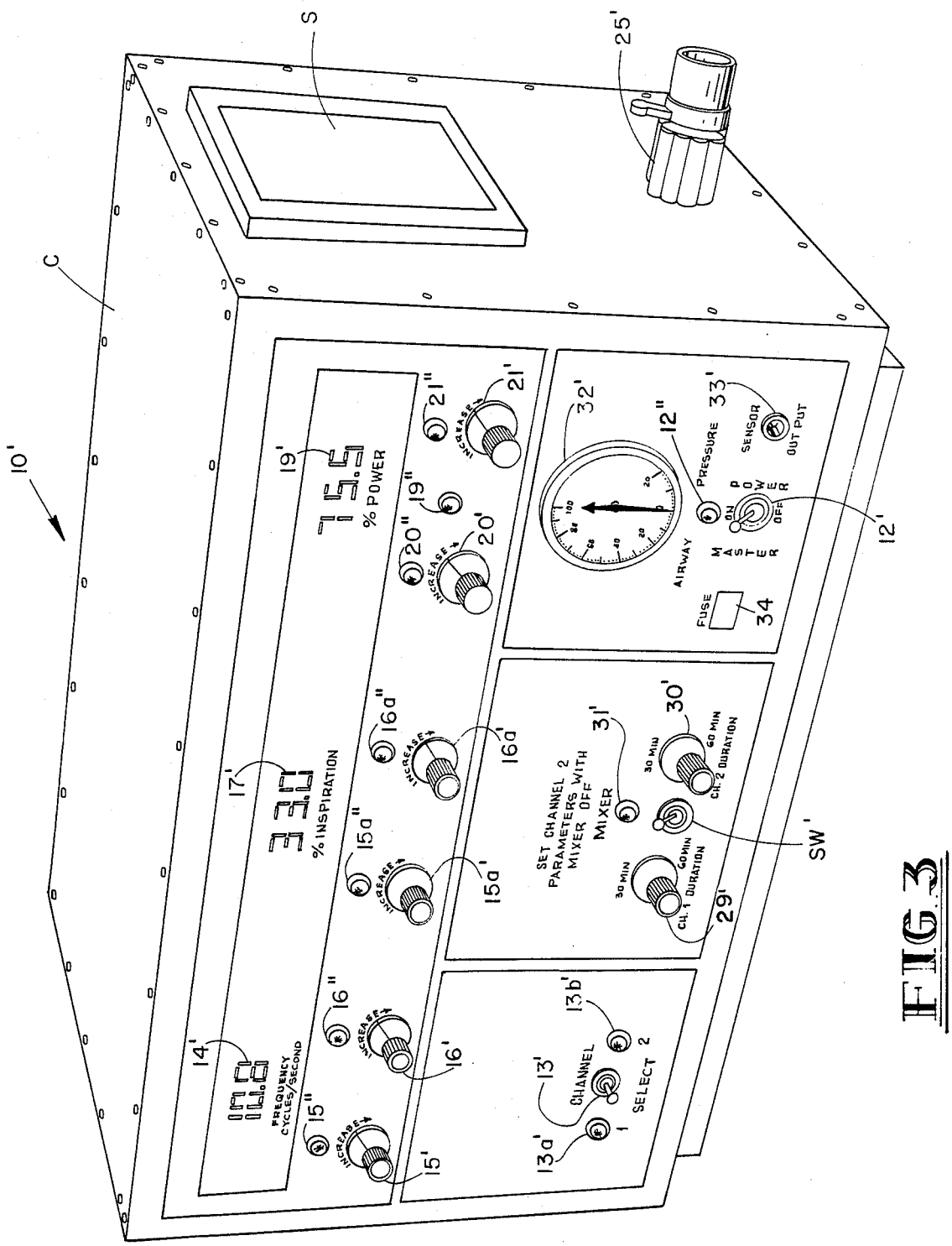
FIG. 3 is a perspective view of a third embodiment of a high frequency ventilator according to the present invention.
Figure 4:
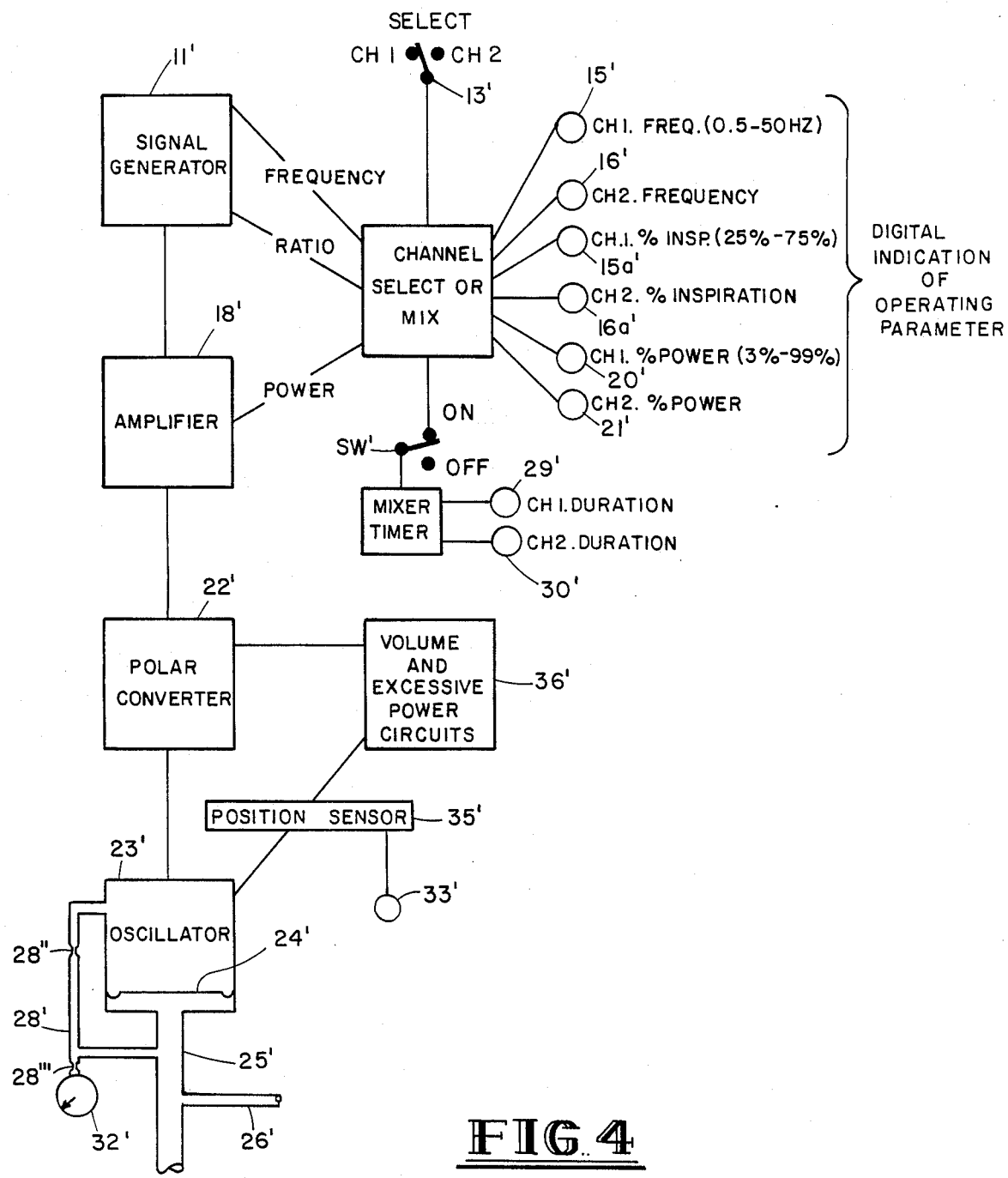
FIG. 4 is a block diagram of the embodiment of the invention shown in FIG. 3.
Figure 10:
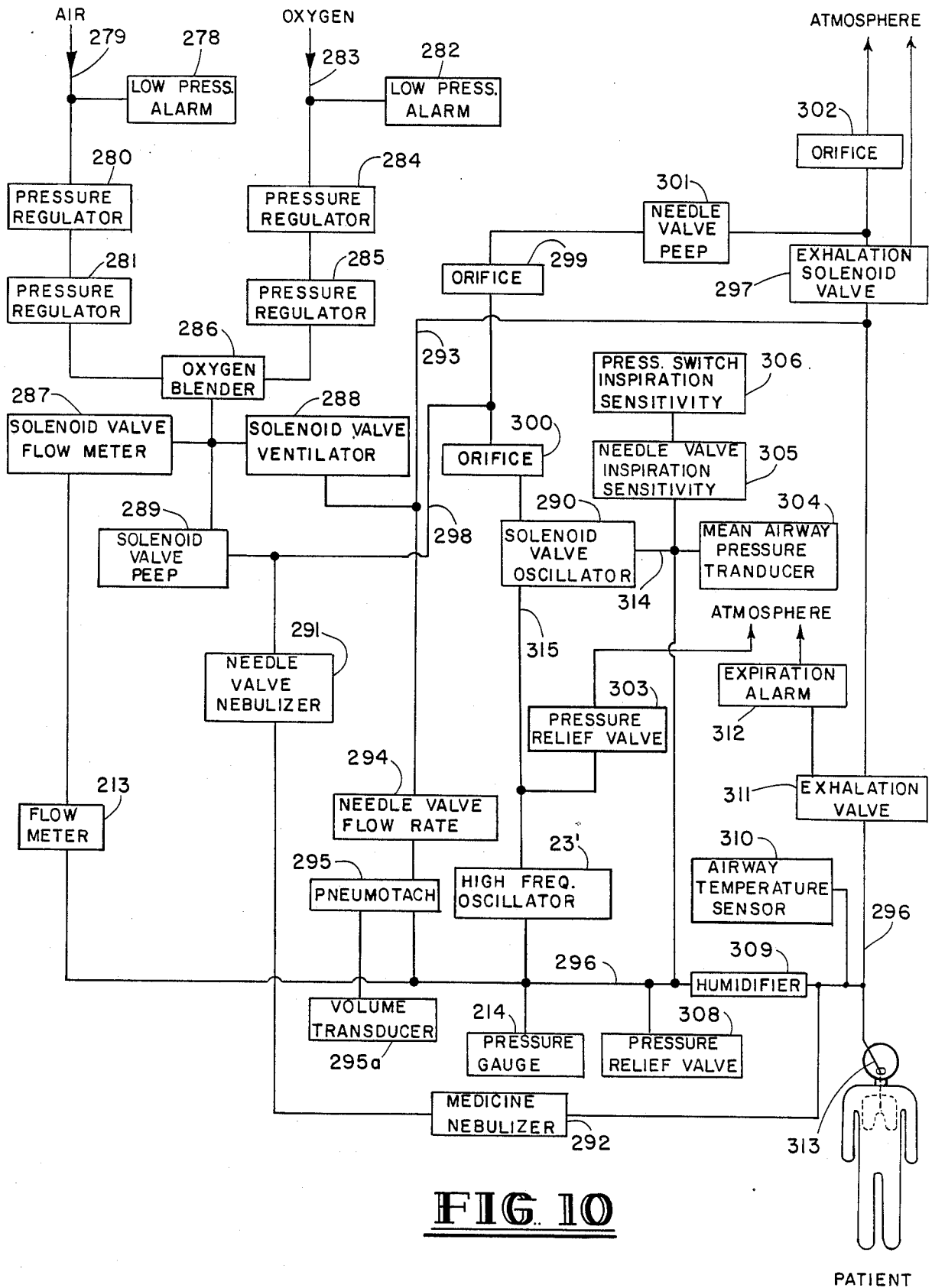
FIG. 10 is a block diagram of the pneumatic circuitry of the present invention.

Referring to FIG. 3 of the drawings, there is shown a perspective view of a high frequency ventilator 10'. The high frequency ventilator 10' includes a signal generator 11' such as shown in FIGS. 1, 10 and 11. When the toggle switch 12' is moved to the on position, power is supplied to the signal generator 11' as shown in FIG. 4. LED indicator light 12' indicates when the system is on. Toggle switch 13' selects one of two channels which may be alternately selected. Digital readout 14' indicates the frequency as a signal generated for the selected channel. The control knobs 15' and 16' set the frequency for the respective first and second channels. The control knobs 15a' and 16a' set the period for the respective first and second channels to control the I:E ratio for the respective first and second chanels. The digital meter 17' shows the inspiration to expiration ratio or the I:E ratio.

Channel 1 on the apparatus is selected by moving the toggle switch 13' to the "1" position which will light up the yellow LED's 12a', 15a", 15''', and 20" above the appropriate control for adjusting channel 1 operation. Similarly channel 2 may be selected by switching the channel selector toggle switch 13' to the "2" position which will light up the yellow LED's 13b', 16" and 21" above the appropriate control for adjusting channel 2 operation.

The percent inspiration can be increased by clockwise rotation of the control knobs 15a' and 16a'. Clockwise rotation of the channel 1 control knob 15a' will lengthen the amount of time with ventilator spends on the positive side of the high frequency stroke in channel 1. Similarly, clockwise rotation of the channel 2 control knob 16a' will lengthen the amount of time the ventilator spends on the positive side of the high frequency stroke in channel 2. The LED indicators 15a" and 16" above the appropriate controls for the control knobs 15 and 16 indicate the channel which is being activated.

The output of the amplifier is shown on digital meter 19' and the power gain is adjusted by control knobs 20' and 21', LED indicators 20" and 21" above the appropriate control knobs 20' and 21' light up to show which channel is being used. An excessive power LED 19" lights when the safe power is exceeded. Clockwise rotation of the channel 1 power control knob 20' will increase the amount of power applied to the high frequency drive shown in FIGS. 5 and 6. Similarly, clockwise rotation of the channel 2 increase control knob 21' will increase the amount of power applied to the high frequency driver. Turning the channel 1 control knob 15' clockwise will increase the ventilator breath rate if the channel selector is in the "1" position. Similarly turning the channel 2 control knob 16' clockwise will increase the ventilator breath rate if the channel selector is in the "2" position.

The sigh function is provided by a sigh timer which is controlled by mixer switch SW' and control knobs 29' and 30'. When the switch SW' is on and the control switch 13' is set on channel 1, the setting of knob 29' provides a first predetermined period of time to elapse during which the system operates on channel 1. At the end of the first predetermined period of time, the sigh timer causes the machine to change to channel 2 for a second predetermined period of time as set by control knob 30'. After the second predetermined period of time has elapsed, the machine reverts to operation on channel 1 for the first predetermined period of time. The system continues cycling between the channels 1 and 2 as long as the switch SW' is in the on position. An LED indicator 31' indicates when the switch SW' is in the on position.

An airway pressure gauge 32' is provided to monitor breathing circuit pressure. The fuse 34 protects the entire machine. The sensor output jack 33' permits connection of an oscilloscope or other measuring device for determining the volume displacement and/or piston or diaphragm position of a linear motor.

Referring to FIG. 4 of the drawings which schematically shows the circuitry of the ventilator 10' there is shown a signal generator 11' having a frequency range of about 45–3000 breaths per minute. The frequency on channels 1 and 2 is about 0.5–50 Hz. The percent inspiration for channels 1 and 2 is about 25%–75%. The percent power range for channels 1 and 2 is about 3%–99%.

The signal produced by the signal generator 11' shown in FIG. 4 is a constant voltage, variable frequency, variable period square wave. This signal passes to an amplifier 18' connected to the signal generator. As discussed above, the power gain for channels one and two is adjusted by control knobs 20' and 21', respectively. The signal generated by the amplifier 18' is directed to a polar converter 22' which is connected to the amplifier. The polar converter 22' serves a dual function of polarizing the square wave and providing the connection between the power supply and the linear motor or oscillator 23'. The linear motor 23' includes a diaphragm 24' which converts mechanical motion to pressure waves in the gas.

Oxygen or compressed gas is added to the system through line 26' which is connected to line 25'. The line 28' allows pressure on both sides of the diaphragms to equalize to the means airway pressure in respirator line 25'. Orifices 28" and 28'" restrict flow to the pressure chamber of the oscillator and pressure gauge 32' respectively. It is understood that the line 25' is connected through suitable medical apparatus to an endotracheal tube or the like to provide breathing function.

The circuits in the system of FIG. 4 can be realized by use of diagrams similar to those of FIGS. 11 and 12, as would be apparent to one of ordinary skill in the art.

The high frequency ventilator 10' shown in FIG. 3 includes a stainless steel cabinet C having a ventilating screen S attached to the side thereof. The high frequency ventilator 10' operates substantially the same as the ventilator 10 shown in FIG. 1 so corresponding reference numerals are used for corresponding components with the addition of a prime ('). Something added to the ventilator as shown in FIGS. 3 and 4 compared to the ventilator shown in FIG. 1 is the position sensor 35', which is explained later, and the volume and excessive power circuit 36', also explained later.

Figure 13:
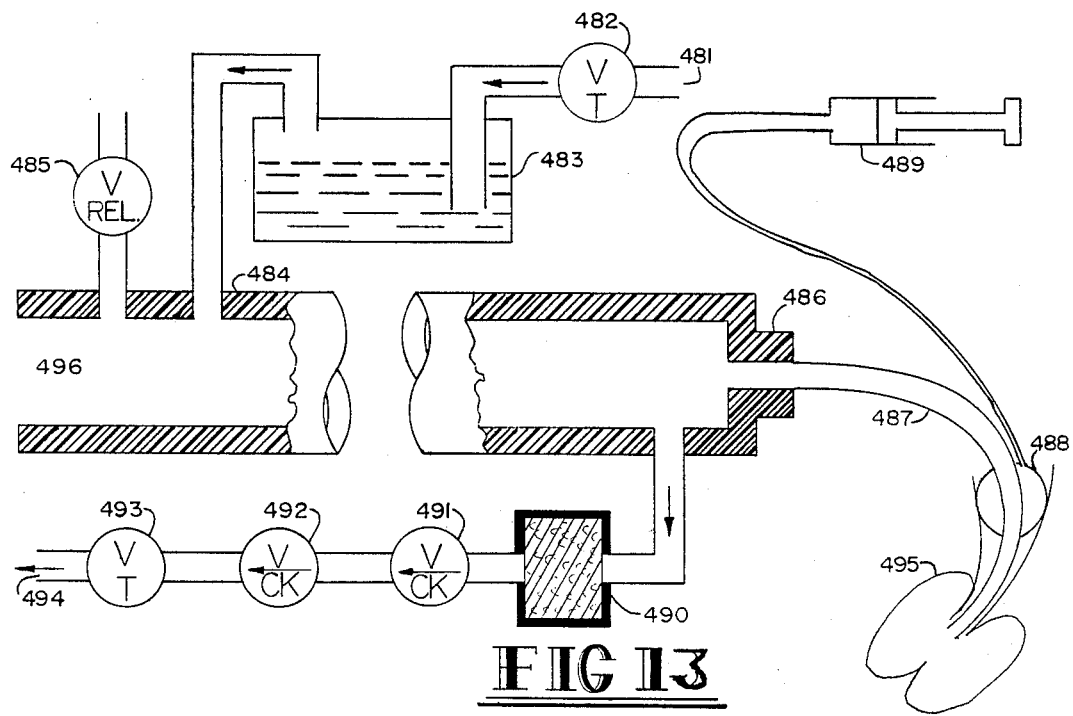
FIG. 13 is a schematic diagram of the connection of the present invention to a patient.

Referring to FIG. 13, which is a schematic representation of an embodiment of the circuit which connects a patient to the invention, the outlet of the machine as shown as 25' on FIG. 3 is connected to point 496. Air, oxygen, anesthesia gas, medicine gas or a combination of gases is introduced into the circuit as point 481. Throttling valve 482 determines the amount of gas introduced. The gas enters humidifier 483 which can be a cascade type of conventional design that bubbles the gas through heated water which heats it and raises its relative humidity to 100%. The gas then enters the connecting tube 484. If the flow is too great for the pre-selected maximum system pressure, relief valve 485 will open thereby venting the excess flow. The gas is available at adapter 486 and may enter a mouthpiece or endotracheal tube 487 as shown. Endotracheal tube 487 has an inflatable cuff 488 which is inflated by syringe 489 to seal the tube 487 in the airway for communication with the lungs of the patient 495. Gas is allowed to exit the system by first passing through filter 490. Since the flow through the system is very little, it would be possible for a bit of mucous or other secretion to obstruct the small passages in throttling valve 493. Therefore, filter 490 provides a large area for any such secretions to collect rendering a hazard from them unlikely. The filter 490 may be a small mesh brass cloth filter. The gas then passes through check valves 491 and 492 which prevent air entrainment during the reverse pulse of the machine. The system pressure is controlled by throttling valve 493 which opens to the atmosphere.

Figure 7:
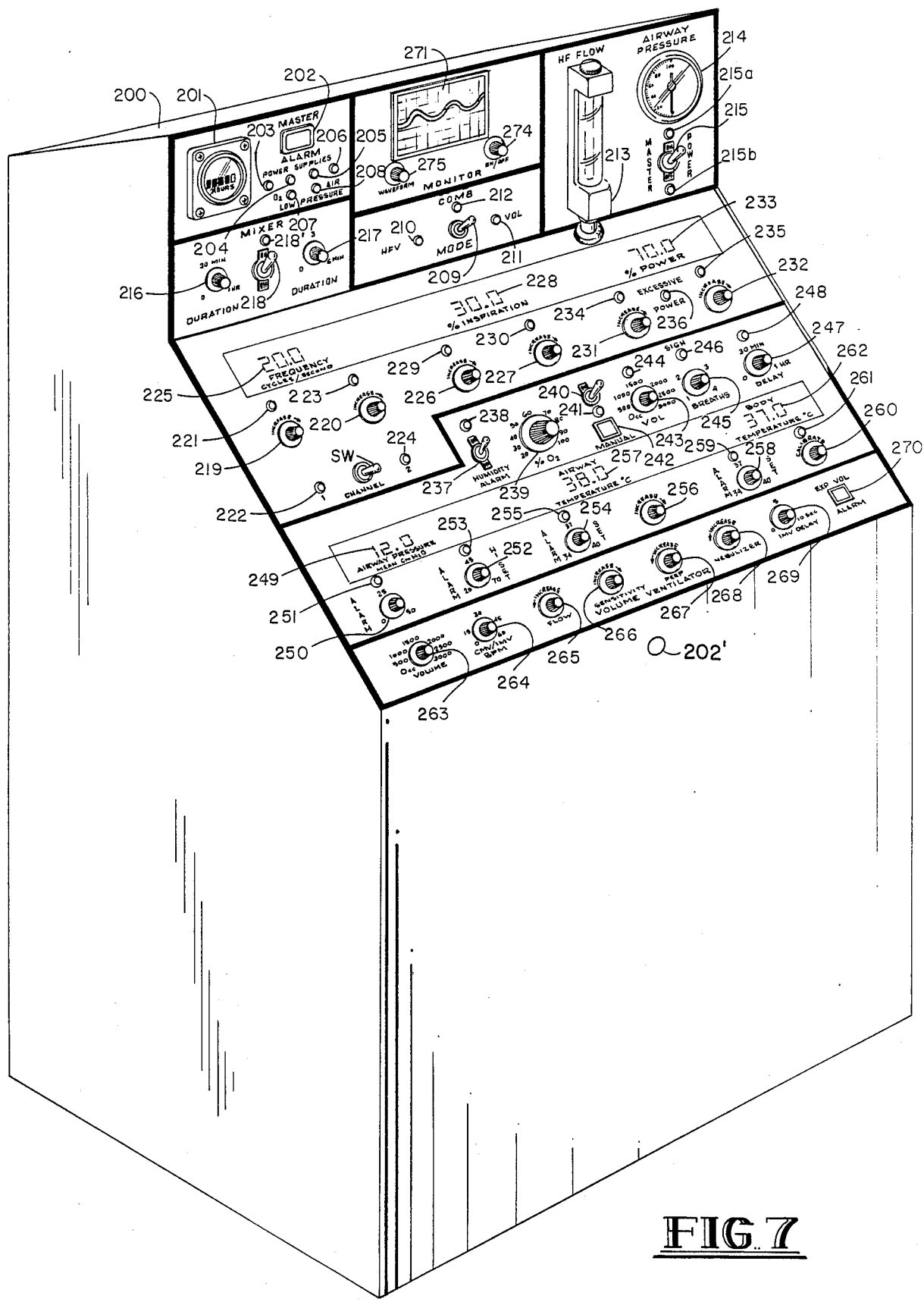
FIG. 7 is a perspective view of an embodiment of the present invention incorporating both a high frequency ventilator and a volume ventilator.
Figure 9:
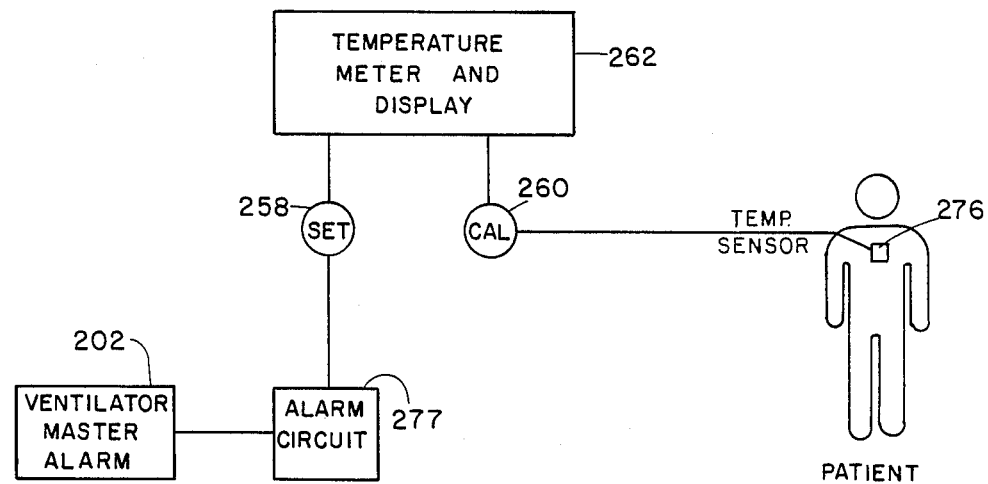
FIG. 9 is a block diagram of a temperature alarm system for use in the present invention.
Figure 8:
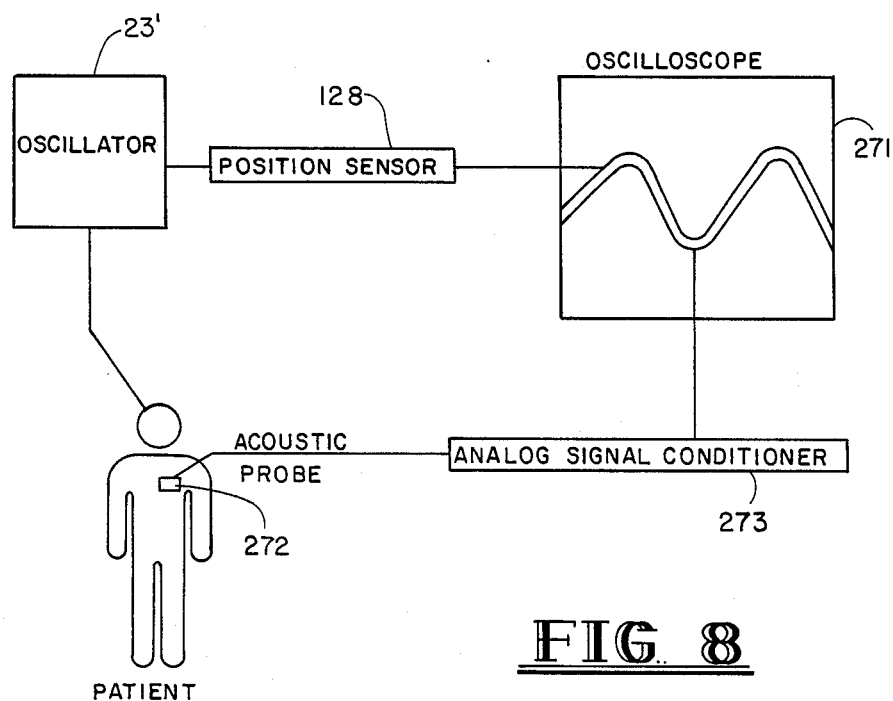
FIG. 8 is a block diagram of the embodiment of the invention shown in FIG. 7.

Referring to FIG. 7 of the drawings there is shown another embodiment of the invention. This embodiment of the invention in addition to including the high frequency ventilator of the invention also includes a volume ventilator. The ventilator includes a cabinet or housing 200 which may be made of stainless steel or other suitable material. The instrumentation on the housing is explained as follows.

An hour meter 201 is provided to record the total operating time. A master alarm light 202 is provided to flash for all alarms and a tone is generated by horn 202'. Alarm lights 203, 204, 205 and 206 flash for malfunction of power supplies. Alarm light 207 flashes when oxygen pressure is falling. Alarm light 208 flashes when the air line pressure is failing. Toggle switch 209 allows selection between the high frequency ventilator, the volume ventilator or a combination of the ventilators. Indicator light 210 indicates when the high frequency ventilator is in operation, indicator light 211 indicates when the volume ventilator is in operation and indicator light 212 indicates when both the high frequency and volume ventilators are in operation.

Thorpe tube flow meter 213 indicates the flow rate adjustment for the high frequency gas entrainment. Airway pressure gauge 214 is used to monitor the breathing circuit pressure. The master power switch 215 turns the machine on and off. LED indicator light 215a indicates when the machine is on. An alarm light 215b and horn may be provided to alert an operator when the switch 215 is turned on and the power source is not connected.

Toggle switch 218 activates the automatic channel selecting circuit. LED indicator light 218' indicates when the channel selector is on. Control knob 216 controls the operation time of channel 1. It provides for the operation of channel 1 up to about 1 hour. A channel 2 duration knob 217 is also provided to control the operation time of channel 2 up to about 6 minutes.

Control 219 increases the channel 1 frequency when rotated in the clockwise direction. Control 220 similarly increases the channel 2 frequency when rotated in the clockwise direction. Indicator lights 221 and 222 indicate operation of channel 1. Indicator lights 223 and 224 indicate operation of channel 2. Digital meter 225 indicates the frequency in cycles per second of the channel which is operating.

Control knob 226 when rotated in a clockwise direction increases the channel 1 percent of inspiration. Similarly control knob 227 when rotated in the clockwise direction increases the channel 2 percent inspiration. Digital meter 228 indicates the percent inspiration for the channel which is operating. Indicator light 229 and 230 indicate the operation of channels 1 and 2 respectively.

Control knob 231 increases the channel 1 drive power when rotated in the clockwise direction. Similarly control knob 232 increases the channel 2 drive power when rotated in the clockwise direction. The percent power is shown on the digital meter 233. Indicator lights 234 and 235 indicate the operation of the first and second channels respectively. Indicator light 236 indicates when the piston is at either extreme of its travel.

Toggle switch 237 switches on a low humidity alarm. Alarm light 238 indicates when the low humidity alarm is tripped. Control knob 239 blends oxygen and air to give a variable percent oxygen. Toggle switch 240 arms the sigh function. Indicator light 241 indicates when the sight function is in progress. Switch 242, when depressed, provides a manual sigh.

Control knob 243 increases the sigh volume when rotated clockwise. Indicator lights 244, 246 and 248 light when the switch 240 is on. Control knob 245 selects the number of sigh breaths for each sigh cycle. Control knob 247 selects the number of sigh cycles per hour. When switch 240 is on the time set by control 247 begins to run. After the set time period expires, control of the entire machine is assumed by the settings on controls 243 and 245. The machine then gives the patient the number of breaths designated by control 245 of the volume designated by control 243 after the completion of which control of the machine is returned to the appropriate mode set by switch 209. The time set by control 247 then begins to run again to repeat the cycle. The manual sigh switch 242 overrides the time delay set by control 247 to cause the sigh function to commence when depressed. When the switch 242 is depressed, and after the sigh cycle is completed, the time delay begins again at zero.

The mean airway pressure digital meter 249 shows the airway pressure in centimeters of water. Control knob 250 sets the low pressure alarm limit which causes alarm light 251 to flash when the low pressure limit has been reached. Control knob 252 sets the high pressure alarm limit and alarm light 253 flashes when the high pressure limit is reached. Control knob 254 sets the airway temperature alarm level and alarm light 255 flashes when the preset temperature range is exceeded. Control knob 256 increases the airway temperature when rotated in the clockwise direction. Digital meter 257 indicates the airway temperature in degrees centigrade.

Control knob 258 sets the body temperature alarm level. Alarm light 259 flashes when the body temperature exceeds the present range. Control knob 260 calibrates the body temperature readout. Indicator light 261 is on when the body temperature monitor is on. Digital meter 262 indicates the body temperature in degrees centigrade.

The hour meter 201 provides continuous monitoring of the instrument operating time. It may be used for recording patient time and four recommended service. The master alarm light 202 illuminates when any alarm function is tripped. This may be a bright red light which flashes in conjunction with an intermittent tone generated by a horn 202 to gain the attention of the attendant in charge. Once the operator has returned to the ventilator he will find that an additional alarm light will be illuminated at the precise location of the function causing the alarm. The following alarms are also installed to insure maximum patient safety. The power supply alarms 202, 204, 205 and 206 when illuminated indicate that a power source for the machine electronics has failed and another machine should be brought in immediately. The oxygen and air low line pressure lights 207 and 208, respectively, are provided to alarm the machine operator that the hospital oxygen or air gas supply has dropped below about 35 PSI. The ventilator will function normally until the pressure is below 25 PSI. Therefore, this gives adequate warning for patient safety. For the humidity alarm, the humidity alarm LED 238 flashes when the relative humidity in the patient's inspired gas drops below safe limits. This notifies the therapist to check the system humidifier and reservoir for proper operation and water supply. For the airway pressure alarm, changes in airway pressure generally occur when either the ventilator or patient have undergone a change that will require immediate attention. Changes in airway pressure that are either high or low could be life threatening so adjustable alarms 250 and 252 have been provided for low and high pressure respectively. The airway temperature alarm provides notice when the inspired gas temperature has gone out of range. Increasing cooling or heating will cause a change in the body's temperature so that monitoring is necessary. The body temperature alarm is provided since airway temperature may cause changes in body temperature. The expired volume alarm 270 is provided to tell the operator if the patient expiration decreases or ceases. When this alarm is activated, there is usually an accidental disconnection of the patient from the ventilator and immediate action is required. Because of urgency, extra light and sound are generated.

When master power switch 215 is on, a green LED 215a above the master switch 215 glows. However, in the event of an AC power failure, the red LED light 215b below the switch 215 will flash accompanied by an intermittent tone from horn 202'.

The mode control switch 209 changes the ventilator from standard breathing to high frequency breathing. Standard breathing rates may also be combined with high frequency rates by moving the mode selector to the combined position. When this is done, the patient may receive the benefit of both ventilators simultaneously.

The high frequency gas flow is controlled by a Thorpe tube flow meter 213. The gas flow rate is adjustable from zero to 15 liters per minute (LPM). Increasing flow provides more fresh air for the patient to breathe. Adequate flow is required or the patient will begin to re-breathe his expired air. A blood gas analysis should be used to determine the patient's oxygen and carbon dioxide level for proper adjustment.

The airway pressure gauge 214 is used to monitor the patient's airway pressure during each cycle of the ventilator. This is a reliable mechanical gauge which may also be used to cross-check the mean airway pressure digital meter 249.

The frequency digital meter 225 provides a precise measurement of the number of cycles per second. The rate may be changed with control knobs 219 and 220 for chanels 1 and 2, respectively. The selector switch SW controls which channel is used. When the high frequency ventilator is operating the LED 221 or 223 lights above the control in use. Increasing frequency generally reduces tidal volume and increases the carbon dioxide level in the blood.

The percent inspiration digital meter 228 provides readout and adjustment for setting the high frequency inspiration versus expiration time. When the machine pushes air forward, it is called inspiration, and when it pulls backward, it is called expiration. Therefore, the amount of time the ventilator works in either direction can be adjusted. LED lights 229 and 230 indicate which control for each of the channels is in use. Varying the ratio of inspiration to expiration causes changes in airway pressure. Also medicine and secretions such as mucous may be transported either into or out of the lungs at certain ratios. This may be used to enhance secretion clearance from the lungs.

The percent power digital meter 233 and the controls 231 and 232 provide readout and adjustment for the amount of drive power applied to the oscillator. The excessive power indicator LED 236 flashes when the piston is at either extreme of its travel. LED lights 234 and 235 designate the control in use. Increase in the operating power reduces the patient's carbon dioxide level in the blood and has little effect on the oxygen level. Therefore, carbon dioxide levels can be changed without changing the oxygen level. The percent oxygen control 239 is used to adjust the percentage of oxygen desired in order to maintain proper oxygenation of the patient. When this control is used oxygen flow leaving the ventilator can be changed to any desired concentration between 21% and 100% oxygen. If the patient's oxygen level is too low an increase with this control will raise his oxygen level.

The sigh module consists of switches 240 and 242, an "in progress" LED light 241 and LED indicator lights 244, 246 and 248 and their controls 243, 245 and 247. The first switch 240 is used to turn on the sigh module. The red push button switch 242, will give a manual sigh when depressed. The volume control 243 is used to adjust the sizes of the breaths from zero to 3 liters. The breaths control knob 245 allows the operator to set the number of breaths from 1 through 4 breather per sigh cycle. The delay control knob 247 is used to adjust the amount of time that will pass before the next sigh cycle will begin. Time is adjustable from zero minute to about 1 hour.

The sigh cycle helps prevent lung collapse. When a patient is ventilated automatically, with a constant volume, his alveoli need to be expanded occasionally. The sigh accomplishes this.

The digital meter 249 provides a pressure reading for the patient's average airway pressure. Because patients can be ventilated at lower pressures using high frequency, an accurate indicator for mean airway pressure is necessary. The operator can use this meter to maintain pressure within safe limits.

The digital meter 257 gives a direct temperature reading in centigrade degrees of the gas going to the patient. Keeping the inspired air at body temperature is required to prevent hypothermia.

The body temperature digital meter 262 displays the patient's body temperature by using a probe 276 placed on the patient's body. The patient's temperature is measured with an ordinary thermometer and that temperature is set on the digital meter with the calibrate control 260. Body temperature can be affected with high frequency ventilation. Therefore, body temperature monitoring is desirable.

The volume control knob 263 found in the volume ventilator section is used to adjust the patient's breath volume from zero to 3 liters per breath. As the breath volume is increased, the patient's oxygen level increases and his carbon dioxide decreases. The continuous mandatory ventilation/intermittent mandatory ventilation (CMV/IMV) control 264 regulates the breaths per minute allowing the operator to select any breath rate between 2 and 60 breaths per minute. Increasing the rate control will increase the patient's ventilation. This causes the patient's oxygen level to rise and his carbon dioxide level to decrease. The flow control knob 265 varies the speed that air flows from the ventilator to the patient during inspiration. This speed is adjustable from zero to 150 liters per minute. Increasing the speed causes inspiration to take less time. This control is normally adjusted to give the patient a comfortable inspiration rate.

The sensitivity control knob 266 adjusts the volume ventilator so that it can operate manually when the patient's efforts to breather are good enough not to need automatic ventilation. Increasing sensitivity makes it easier for the patient to breather on his own. The positive end expiratory pressure/continuous positive airway pressure (PEEP/CPAP) are adjustable from 1 to 50 centimeters of water. This is the residual pressure in the lungs at the end of expiration by the patient. It is required when a patient is in danger of a lung collapse or it recovering from one. Use of PEEP or CPAP means that the air pressure inside the patient's lungs is always kept above zero, thereby holding them open. The nebulizer control 268 varies the medicine aerosolization rate to the patient. The more it is increased the faster to patient receives his medicine. The intermittent mandatory ventilation delay (IMV delay) is controlled by knob 269. When the policy to have an automatic takeover in case of relapse; it is also wise to give him a synchronized breath (with his own) at a given interval. The control knob 269 allows the machine to search for up to 10 seconds for a patient inspiration before it cycles on its own.

The volume ventilator section is as follows. Control knob 263 increases the tidal volume. Control knob 264 increases the CMV/IMV breaths per minute. Control knob 265 increases the inspirator flow rate and decreases the inspiratory time when rotated counterclockwise. Control knob 266 increases the sensitivity of the volume ventilator to the inspiratory effort when rotated in the clockwise direction. Control knob 267 increases the PEEP/CPAP pressure when rotated in the counterclockwise direction. Control knob 268 increases the medicine nebulizer flow when rotated in the counterclockwise direction. Control knob 269 increases the IMV search time for patient inspiration when rotated in the clockwise direction. Alarm light 270 lights to alarm for loss of patient expiration.

The common section of the high frequency and volume ventilators is composed of accessory components that are used during either high frequency or volume ventilation. These include the following:
1. Humidity Alarm
2. Low Airway Pressure Alarm
3. High Airway Pressure Alarm
4. Airway Temperature Alarm
5. Body Temperature Alarm
6. Air and Oxygen Blender
7. Manual and Automatic Sigh
8. Digital Displayed Mean Airway Pressure
9. Digital Displayed Airway Temperature
10. Airway Temperature Control
11. Digital Displayed Body Temperature
12. Body Temperature Calibrate The humidity alarm utilizes an electronic sensor to analyze the water vapor content of the inspired air passing from the main stream humidifier to the patient. The humidity alarm chamber contained in the high frequency ventilator is updated on a continuous basis during high frequency ventilation and breath by breath during volume ventilation. The alarm is scaled to activate when relative humidity drops below about 80%. The alarm may be turned on and off with the humidity alarm toggle switch 237.

The low airway pressure alarm is used to monitor minimum airway pressure during high frequency and volume ventilation. The alarm is adjustable from about zero through 50 centimeters of water. When the alarm is tripped, a warning sound and a warning light 251 are activated to draw attention to the control.

The high airway pressure alarm is used to monitor maximum airway pressure during high frequency and volume ventilation. The alarm is adjustable from about 20 through 70 centimeters of water. When the alarm is tripped, a warning sound and a warning light 253 are activated to draw attention to the control.

The airway temperature alarm is used to monitor airway temperature during high frequency and volume ventilation. The alarm is adjustable from about 34° Centigrade to 40° Centigrade. When the alarm is triggered, a warning sound and a warning light 255 are activated to draw attention to the control.

The body temperature monitor is used to monitor body temperature during high frequency and volume ventilation. The alarm is adjustable from 34° Centigrade through about 40° Centigrade. When the alarm is triggered, a warning sound and a warning light 259 are activated to draw attention to the control.

The air and oxygen blender 239 is a dual mixture control capable of delivering 200 LPM flow rates and concentrations form 21% to 100% oxygen. The system incorporates dual alarms for air and oxygen low line pressure which when activated emit a warning sound and warning lights 207 or 208 to notify the operator of the problems.

The manual and automatic sigh module controls the patient's sighing. There are variable controls for tidal volume, number of breaths per sigh and sigh delay interval. The tidal volume control 243 is adjustable from zero cc's to 3,000 cc's. The breaths control knob 245 is adjustable from 1 to 4 breaths per sigh. The delay control knob 247 is adjustable between zero minutes and 1 hour. When the sigh toggle switch 240 has been turned on, the lights 244, 246 and 248 will be illuminated to indicate that the sigh module has been activated. To test the sigh or to manually sigh the patient, you need merely press the manual red push button 242 to interrupt the set high frequency or volume ventilation and begin to cycle. Once the sigh program has been completed, the high frequency or volume ventilator will return to normal operation and the light 241 will go out. The digital display 249 for the mean airway pressure is used for reading airway pressure changes during high frequency or volume ventilation. The internal transducer also combined with the low and high airway pressure alarms to monitor the maximum and minimum airway pressures.

The digital display 257 for airway temperature is used to monitor end airway temperature. The airway temperature sensor 310 is placed near the patient's mouthpiece so that an accurate temperature is monitored.

The airway temperature control 256 located below the digital display 257 is used to adjust the humidifier temperature to raise or lower the airway temperature. The digital display 262 for body temperature displays the patient's body temperature. A body temperature sensor 276 is placed somewhere on the body and the patient's temperature is taken manually. The body temperature calibration control 260 is used to set in the patient's body temperature after which the digital display will track the changes in body temperature. During high frequency and volume ventilation care must be taken to prevent hypothermia.

The volume ventilator is a pneumatically powered and electronically governed volume ventilator. It is capable of delivering smooth inspiratory power at flow rates up to 200 LPM and pressures up to 120 centimeters of water.

The volume ventilator has an electronic or pneumatic controls for the following functions:
1. Tidal "Volume"
2. "CMV/IMV" Rate
3. Inspiratory "Flow"
4. Patient "Sensitivity"

5. "PEEP" (Positive End Expiratory Pressure)
6. "Nebulizer" flow rate
7. "IMV Delay"

The ventilator also incorporates an expired volume alarm 270. The volume control 263 governs the size of the tidal volumes which are delivered by the ventilator. The sizes of these breaths can range from zero cc's to 3,000 cc's. The CMV/IMV breaths per minute control 264 is used to regulate the number of breaths per minute being delivered to the patient. The control is used for either continuous mandatory or intermittent mandatory ventilation.

The inspiration flow control know 265 regulates the speed at which air travels from the ventilator to the patient. The maximum inspiration flow rate is approximately 200 LPM.

The patient sensitivity control knob 266 is used to regulate the necessary effort required by the patient to activate the ventilator. This effort may be overriden or adjusted as sensitive as 0.5 centimeters of water.

The PEEP valve which is controlled by control knob 267 is used to control end expiratory pressure during volume ventilation and for adjusting mean airway pressure during high frequency ventilation. The nebulizer flow rate control knob 268 regulates flow to the medicine nebulizer. Increase in the flow will generate an increase in medicine to the patient. The IMV delay control 269 is used to help synchronize the IMV breath with the patient's actual breathing. The IMV delay can be set to search for up to 10 seconds before inflating the patient's lungs. IMV delay is intended to reduce the risk of inflating the patient during a normal expiration.

The expired volume alarm light 270 and interconnected expired volume alarm horn are used to detect the loss of exhalation from the patient. When the expired volume alarm is triggered the master alarm light 202 and the expired volume light 270 are illuminated. Also the master alarm horn 202' and the expired volume alarm horn are activated. The master alarm light 202 and horn 202' and the expired volume alarm light 270 and horn will operate intermittently and out of phase to increase maximum notice.

The high frequency ventilation may be coupled with aerosol therapy for benefits in two areas. The first area is in particle distribution. Aerosol particles introduced into the lungs tend to be deposited rather than exhaled when coupled with high frequency ventilation. Certain percent inspirations will cause aerosol droplets forming in the endotracheal tube to move down the tube and into the lungs. The second area is in mucocilliary clearance. At certain percent inspirations the ventilator will cause liquid outflow from the lungs. Mucous can be removed from a lung into the ET tube and subsequently out of the patient.

The high frequency oscillator piston position is sensed by the piston sensor 228. The signal from the position sensor is fed into one channel of an oscilloscope 271 shown in FIGS. 7 and 8. The acoustic probe 272 picks up the vibration in the patient's chest and the analog signal conditioner 273 feeds the other channel of the oscilloscope. The controls of the oscillator are then varied until both signals are in phase with one another. This allows rapid establishment of optimum oscillator parameters to overcome asympathetic harmonic vibrations in the airways which inhibit ventilation. This method may be used as an internal component of a high frequency ventilator or as an external system. Control knob 274 is provided to turn the oscilloscope 271 on and off. The display mode volume wave form is determined by control knob 275.

The patient's body temperature is monitored as shown in FIG. 9. A temperature sensor 276 is provided for connecting with the patient. The calibrate control knob 260 adjusts the monitor to the temperature measured conventionally. The control knob 258 turns the monitor on and sets the alarm. The monitor tracks the body temperature. If the temperature varies plus or minus one degree Centigrade, the alarm circuit 277 triggers the ventilator master alarm 202 to alert the operator. The sensor 276 is the only external component. The advantages of the temperature meter and display are that they provide real time constant temperature display, it is integrated with the ventilator, the alarm may be used for rise or fall of temperature, it monitors the ventilator as well as the patient and the non-intrusive sensor 276 may be taped to the body of the patient.

Pneumatic circuitry of the ventilator is schematically shown in FIG. 10. The device includes a low pressure alarm 278 connected to the air inlet line 279. Regulators 280 and 281 are provided to control the incoming air. A low pressure alarm means 282 is connected to the oxygen inlet line 283. Regulators 284 and 285 are connected to the oxygen line. The air and oxygen lines are in turn connected to an oxygen blender 286 controlled by knob 239. The oxygen blender is connected to solenoid valve flow meter 287 and the solenoid valve 288 which goes to the ventilator. The oxygen blender 286 is also connected to solenoid valve 289. Solenoid valve 289 controls the positive end expiratory pressure (PEEP). A flow meter 213 receives flow from the solenoid valve 287. A needle valve nebulizer 291 controlled by knob 268 is provided to receive flow from the solenoid valve 289. A medicine nebulizer 292 is provided for nebulizing medicine. Solenoid valve 288 is connected to line 293 which goes to a needle valve 294 for regulating the flow rate. The needle valve 294 is in turn connected to pneumotach 295. The pneumotach 295 is connected to a volume transducer 295a which gives an electronic signal to close the solenoid valve 288. The pneumotach 295 is also connected to the airway line 296. The line 293 is connected to exhalation solenoid valve 297 which exhausts to the atmosphere. The solenoid valve 289 is connected through line 298 to orifices 299 and 300. The orifice 299 goes to a needle valve 301 controlled by knob 267 which goes to the orifice 302 which exhausts to the atmosphere. The orifice 300 goes to the solenoid valve 290 for the oscillator 23'. A pressure relief valve 303 is provided to exhaust to the atmosphere. The three-way solenoid valve 290 is connected to the mean airway transducer 304 which gives an electronic signal for the mean airway pressure. A needle valve 305 controlled by knob 266 is provided for the inspiration sensitivity. Pressure switch 306 is also provided for the inspiration sensitivity. The high frequency oscillator 23' is connected to pressure gauge 214. Pressure release valve 308 is also provided to relieve excess pressure. A conventional humidifier 309 is provided in the airway line. The airway temperatures sensor 310 detects the temperature in the airway. An exhalation valve 311 is provided and is closed by pressure. The exhalation valve 311 is connected to the expiration alarm 312 which is vented to the atmosphere. The airway line 296 is connected to an endotracheal tube 313 which goes down the throat of the patient and into the airway into the bronchial tubes.

When the mode switch is in the high frequency position, the solenoid valve 287 is open (only time it is open). When the mode switch is in the combination position, solenoid valve 287 closes, solenoid valve 288 opens, and solenoid valve 289 opens.

When the mode switch is on the volume only position, solenoid valves 288 and 289 are open. Lines 314 and 315 are connected by the three-way solenoid valve 290.

The high frequency ventilator of the invention has been designed to operate in a variety of configurations which will enhance ventilation and oxygenation above the levels of current technology. The ventilator has been designed to cover a wide degree of variable yet operate with simple, predictable and minimal controls. The ventilator is also constructed to withstand the abuse that it will receive while in hospital use.

EXPERIMENTAL TEST RESULTS

The high frequency ventilator of the present invention has been tested at major medical facilities and shown effective in four major applications. They are:
(1) Mucociliary transport and secretion and medicine transport. The machine has been shown to effectively cause substances to be moved out of or into the lungs depending upon the therapist's desires.
(2) Acute respiratory failure. The machine has been shown to be a safe and effective ventilatory means for maintaining life after severe lung injuries.
(3) Hayline Membrane Disease. The machine has been shown to provide a safe and effective means for respiration of infants with HMD.
(4) Anesthesia Delivery. The machine has been shown to be a safe and economical means for delivery of anesthesia and enhancing the recovery process during surgical procedures and other procedures requiring general anesthesia.

During eleven experiments, mongrel dogs weighting 20 to 40 Kg were chronically instrumented with endocordial crystals implanted in the left and right ventricles of the heart to evaluate the shape changes of the ventricles during high frequency ventilation. The dogs were acutely anesthetized and paralyzed and placed on high frequency ventilation at 20 Hz to 30 Hz, 50% inspiration and power as required for proper $CO_2$ elimination with 5 liters per minute airflow and $FIO_2$ (fraction of inspired $O_2$)+1.0. Mean airway pressures were varied from 4 to 40 cm $H_2O$ and heart dimensions were recorded. The machine provided ventilation during these experiments.

The machine was used during various surgical and anesthesia procedures on 14 dogs and 4 cats at frequencies ranging from 5 to 50 Hz and at various % inspirations. The procedures and results are as follows:
(1) Gut resection, 60 lb doberman dog. Intestinal blockage diagnosed 3 weeks prior to procedure and deemed to be a very high surgical and anesthesia risk. The machine was combined with an Ohio anesthesia machine to deliver Metafane gas. The patient was ventilated for 1 hour 40 minutes at 30 Hz and recovered uneventfully.
(2) Dental prophylaxis, 5 lb, 10 year old Dachshund male dog. The patient was entubated and paralyzed with succinylcholine at 20 Hz during the procedure and recovered normally.
(3) Dental prophylaxis, 15 lb, 14 year old Schnauzer male dog. Same as 2 above except ventilation period was 1 hour and 5 minutes.
(4) Panhysterectomy, feline, 5 lbs. The machine was used to deliver Metafane gas from an Ohio anesthesia machine. The patient was ventilated at 30 Hz for 30 minutes and has an uneventful recovery with said day discharge.
(5) Umbilical hernia repair, 1 lb English Sheep Dog, 2 weeks old. Delivered Metafane gas from an Ohio anesthesia machine. The patient was ventilated at 15 Hz for 5 minutes, 50 Hz for 15 minutes and 15 Hz for 5 minutes and had an uneventful recovery.
(6) Same as (5) above.
(7) Dental prophylaxis and granulomatous keratatis, 40 lb Toy Poodle, 11 years old. Delivered Metafane gas for ventilation and anesthesia during procedures. Patient was ventilated at 30 Hz for 15 minutes with an uneventful recovery.
(8) Panhysterectomy, 20 lb mongrel dog. Ventilation and anesthesia using Metafane gas during procedure. Patient was ventilated at 30 Hz for 15 minutes, 20 Hz for 10 minutes and had an uneventful recovery.
(9) Panhysterectomy, 35 lb mongrel dog. The machine was used to delivery Metafane gas for anesthesia and to provide ventilation during the procedure. The patient was ventilated at 30 Hz for 20 minutes and 5 Hz for 2 minutes and had an uneventful recovery.
(10) Lipoma, 10 lb Poodle, 13 years old male. Metafane used for anesthesia. The patient was ventilated at 20 Hz for 20 minutes and at 5 Hz for 5 minutes. Recovery was uneventful.
(11) Panhysterectomy, 35 lb dog. The machine was used to deliver Metafane gas for anesthesia and to provide ventilation during the procedure. The patient was ventilated at 5 Hz for 5 minutes, 20 Hz for 5 minutes, 30 Hz for 10 minutes and 5 Hz for 2 minutes. The recovery was uneventful.
(12) Panhysterectomy, 6 lb feline. The machine was used to delivery Metafane gas for anesthesia and to provide ventilation during the procedure. The patient was ventilated at 30 Hz for 10 minutes, 20 Hz for 10 minutes and 5 Hz for 5 minutes. The recovery was uneventful.
(13) Panhysterectomy, 5 lb feline. Similar to (12) above except that ventilation was at 30 Hz for 20 minutes with an uneventful recovery.
(14) Multiple mammary carcinoma excisions and panhysterectomy, 65 lb Afghan Hound. The machine was used to deliver Metafane gas for anesthesia and to provide ventilation during the procedures. The patient was ventilated at 20 Hz for 20 minutes, 5 Hz for 5 minutes, 20 Hz for 15 minutes and 5 Hz for 3 minutes. The recovery was uneventful.
(15) Panhysterectomy, 3 lb feline. Similar to (12) above except that ventilation was at 20 Hz for 20 minutes with an uneventful recovery.
(16) Lipoma and holodendron cauterization, 10 lb miniature Schnauzer. The machine was used to deliver Metafane gas for anesthesia and to provide ventilation during the procedures. The patient was ventilated at 20 Hz for 15 minutes and 5 Hz for 10 minutes. Recovery was normal.
(17) Multiple mammary adenocarcinoma excisions, 2 lb Yorkshire Terrier. The machine was used to deliver Metafane gas and to provide ventilation. The patient was ventilated at 20 Hz for 15 minutes and 5 Hz for 5 minutes. Recovery was normal.
(18) Panhysterectomy, 3 lb Poodle. The machine was used to delivery Metafane gas for anesthesia and to provide ventilation at 20 Hz for 15 minutes and at 5 Hz for 5 minutes. Recovery was normal.

Another series of experiments were performed to determine if oleic acid injury dogs could be ventilated by high frequency oscillation.

Fifteen dogs of about 9 Kg weight were anesthetized and treated with oleic acid. After 1 hour of unassisted breathing, they were ventilated by the machine for 4 hours. After each experiment was concluded, additional frequencies, % inspirations and power settings were used to establish ventilatory parameters.

Typical blood gases for the first four animals were as follows:

Another experimental series was conducted on 3 dogs to determine if blood gas values are maintained during a full range of frequency, % I and power settings. Methods and results summaries are as follows:

(1) The dog was anesthetized with surital. The animal was placed on the ventilator for two hours and received 40% humidified oxygen, blood pressure, esophageal pressure, ECG, end tidal $O_2$ and $CO_2$ were continuously monitored. Ventilator settings were 5 and 15 Hz, Full Power and I:E ratios of 55:50, 70:30 and 30:70.

Results:
(a) The dog was well ventilated.
(b) Blood gas analysis was done for each setting.
(c) In all cases $PO_2$ remained high and $PCO_2$ was low.

| DOG | Hz | % I (inspirated) | % P (power) | FIO$_2$ (fraction of inspired O$_2$) | pH (of blood) | PaCO$_2$ (arterial pressure of CO$_2$ in cm H$_2$O) | PaO$_2$ (arterial pressure of O$_2$ in cm H$_2$O) |
|---|---|---|---|---|---|---|---|
| \multicolumn{8}{c}{1 HOUR AFTER OLEIC ACID} |
| 1 | \multicolumn{3}{c}{NORMAL BREATHING} | .65 | 7.32 | 43 | 57 |
| 2 | \multicolumn{3}{c}{NORMAL BREATHING} | .48 | 7.30 | 38 | 73 |
| 3 | \multicolumn{3}{c}{NORMAL BREATHING} | .86 | 7.29 | 46 | 63 |
| 4 | \multicolumn{3}{c}{NORMAL BREATHING} | .81 | 7.14 | 51 | 91 |
| \multicolumn{8}{c}{1 HOUR ON HFV (HIGH FREQUENCY VENTILATION)} |
| 1 | 10 | 33 | 75 | .37 | 7.30 | 41 | 124 |
| 2 | 10 | 33 | 75 | .32 | 7.34 | 39 | 135 |
| 3 | 10 | 33 | 75 | .36 | 7.29 | 42 | 117 |
| 4 | 10 | 33 | 75 | .34 | 7.28 | 34 | 100 |
| \multicolumn{8}{c}{2 HOURS ON HFV} |
| 1 | 10 | 33 | 65 | .37 | 7.35 | 36 | 113 |
| 2 | 10 | 33 | 75 | .32 | 7.28 | 41 | 130 |
| 3 | 10 | 33 | 55 | .35 | 7.30 | 37 | 130 |
| 4 | 10 | 33 | 45 | .35 | 7.28 | 33 | 139 |
| \multicolumn{8}{c}{3 HOURS ON HFV} |
| 1 | 10 | 33 | 65 | .38 | 7.36 | 29 | 100 |
| 2 | 10 | 33 | 65 | .32 | 7.34 | 41 | 89 |
| 3 | 10 | 33 | 65 | .37 | 7.30 | 35 | 126 |
| 4 | 10 | 33 | 65 | .34 | 7.16 | 37 | 127 |
| \multicolumn{8}{c}{4 HOURS ON HFV} |
| 1 | 10 | 33 | 65 | .38 | 7.29 | 34 | 161 |
| 2 | 10 | 33 | 65 | .26 | 7.31 | 42 | 101 |
| 3 | 10 | 33 | 65 | .36 | 7.32 | 36 | 95 |
| 4 | 10 | 33 | 65 | .34 | 7.24 | 45 | 80 |
| \multicolumn{8}{c}{5th HOUR EXPERIMENTS} |
| 1 | 5 | 33 | 80 | 1.0 | 7.55 | 18 | 450+ |
|   | 10 | 33 | 80 | 1.0 | 7.50 | 22 | 450+ |
|   | 15 | 33 | 80 | 1.0 | 7.50 | 25 | 450+ |
|   | 20 | 33 | 80 | 1.0 | 7.45 | 35 | 450+ |
|   | 25 | 33 | 80 | 1.0 | 7.35 | 45 | 450+ |
|   | 30 | 33 | 80 | 1.0 | 7.25 | 50 | 450+ |
|   | 35 | 33 | 80 | 1.0 | 7.15 | 55 | 450+ |
|   | 40 | 33 | 80 | 1.0 | 7.05 | 65 | 450+ |
|   | 45 | 33 | 80 | 1.0 | 7.00 | 75 | 450+ |
|   | 50 | 33 | 80 | 1.0 | 6.95 | 90 | 450+ |
| 2 | 5 | 50 | 80 | 1.0 | 7.55 | 18 | 450+ |
|   | 10 | 50 | 80 | 1.0 | 7.50 | 22 | 450+ |
|   | 15 | 50 | 80 | 1.0 | 7.49 | 24 | 450+ |
|   | 20 | 50 | 80 | 1.0 | 7.47 | 32 | 450+ |
|   | 25 | 50 | 80 | 1.0 | 7.40 | 35 | 450+ |
|   | 30 | 50 | 80 | 1.0 | 7.35 | 45 | 450+ |
|   | 35 | 50 | 80 | 1.0 | 7.25 | 55 | 450+ |
|   | 40 | 50 | 80 | 1.0 | 7.15 | 60 | 450+ |
|   | 45 | 50 | 80 | 1.0 | 7.10 | 70 | 450+ |
|   | 50 | 50 | 80 | 1.0 | 7.00 | 80 | 450+ |
| 3 | 5 | 75 | 80 | 1.0 | 7.45 | 35 | 450+ |
|   | 10 | 75 | 80 | 1.0 | 7.40 | 40 | 450+ |
|   | 15 | 75 | 80 | 1.0 | 7.35 | 45 | 450+ |
|   | 20 | 75 | 80 | 1.0 | 7.30 | 50 | 450+ |
|   | 25 | 75 | 80 | 1.0 | 7.25 | 55 | 450+ |
|   | 30 | 75 | 80 | 1.0 | 7.20 | 60 | 450+ |
|   | 35 | 75 | 80 | 1.0 | 7.10 | 65 | 450+ |
|   | 40 | 75 | 80 | 1.0 | 7.00 | 75 | 450+ |
|   | 45 | 75 | 80 | 1.0 | 6.95 | 85 | 450+ |
|   | 50 | 75 | 80 | 1.0 | 6.90 | 100 | 450+ |

(2) The dog was anesthetized with surital and placed on the ventilator for two hours. The animal received 40% humidified oxygen. Blood pressure esophageal pressure and end tidal 02 and $CO_2$ were monitored. A full range of frequency settings and I:E ratios were used at full power.
Results:
(a) The dog was well ventilated throughout the experiment.
(b) The capabilities of the ventilator were demonstrated.

(3) A dog was anesthetized with surital and paralyzed with curare. The animal was placed on the ventilator for two hours. Blood pressure, esophageal pressure, ECG and rectal temperature was monitored. The animal was on a high impedance bias flow circuit and received 100% humidified oxygen.
Results:
(a) The dog was well ventilated throughout the course of the experiment.
(b) The animal was ventilated at 5 Hz, Full power and I:E ratio of 50:50.

Another experiment series was conducted on 6 dogs to study the effect of different % Inspiration settings on tracheal transport rates methods and results summaries are as follows:

(1) A dog was anesthetized with surital and paralyzed with curare. The animal was placed on the ventilator for three hours and received 100% humidified oxygen. Blood pressure, esophageal pressure, ECG, rectal temperature and end tidal $CO_2$ were continuously monitored. Several time during the study a droplet of radioactive iron oxide was installed in the trachea and its movement was monitored with a tracheal probe and recorded.
Results:
(a) The dog was well ventilated throughout the course of the experiment.
(b) The animal was ventilated at 5 Hz, full power and I:E ratios of 50:50, 70:30 and 30:70.
(c) In all cases mucus moved up the trachea.

(2) A dog was anesthetized with surital and paralyzed with curare. The animal was placed on the ventilator using a high impedance bias flow circuit for approximately 2 hours and received 75% humidified oxygen. Blood pressure, esophageal pressure, ECG, rectal temperature and end tidal $CO_2$ and $O_2$ were monitored. Several times during the study a droplet of radioactive tagged iron oxide was instilled in the trachea and its movement was recorded by means of a tracheal probe.
Results:
(a) The dog was well ventilated throughout the course of the experiment.
(b) The animal was ventilated at 5 and 10 Hz, full power and I:E ratios of 50:50, 70:30 and 30:70.
(c) This was a large animal and suction in the bias flow circuit was not adequate.
(d) There was difficulty keeping the dog under anesthesia.
(e) Because of these difficulties no tracheal rates were recorded.

(3) A dog was anesthetized with surital and paralyzed with curare. The animal was placed on the ventilator using a newly constructed high impedance bias flow circuit for three hours and received 40% humidified oxygen. Blood pressure, esophageal pressure, ECG, rectal temperature, and end tidal $CO_2$ and $O_2$ were continuously monitored. Several times during the study a droplet of radioactive tagged iron oxide was instilled in the trachea and its movement was recorded.
Results:
(a) The dog was well ventilated throughout the course of the experiment.
(b) The animal was ventilated at 10 Hz, full power and I:E ratios of 50:50, 70:30 and 30:70
(c) In all cases mucus moved up the trachea (4) A dog was anesthetized with surital and placed on the ventilator for 2 hours. a high impedance bias flow circuit was used and the animal received 40% humidified oxygen. Blood pressure, esophageal pressure, ECG, rectal temperature and end tidal O2 and $CO_2$ were monitored. Several times during the study a droplet of radioactive tagged iron oxide was instilled in the trachea and its movement was recorded.
Results:
(a) The dog was well ventilated throughout the experiment.
(b) The animal was ventilated at 5 Hz, Full power and I:E ratios of 50:50 and 70:30
(c) Mucus moved up the trachea.

(5) A dog was anesthetized with surital and placed on the ventilator for 3 hours. A high impedance bias flow circuit was used and the animal received 40% humidified oxygen, blood pressure, esophageal pressure, ECG, rectal temperature and end tidal O2 and $CO_2$ were monitored. Several times during the study a droplet of radioactive tagged iron oxide was instilled in the trachea and its movement was recorded.
Results:
(a) The dog was well ventilated throughout the experiment.
(b) The animal was ventilated at 5 Hz, Full power and I:E ratios of 50:50, 70:30 and 30:70
(c) Mucus moved up the trachea.

(6) A dog was anesthetized with surital and placed on the ventilator for 2 hours. A high impedance bias flow circuit was used and the animal received 40% humidified oxygen, blood pressure, esophageal pressure, ECG, rectal temperature and end tidal O2 and $CO_2$ were monitored. Several times during the study, a droplet of radioactive tagged iron oxide was instilled in the trachea and its movement was recorded.
Results:
(a) The dog was well ventilated throughout the course of the experiment.
(b) The animal was ventilated at 10 Hz, Full power and I:E ratio of 70:30 and 25:75.
(c) In all cases mucus moved up the trachea.

Another experimental series was conducted to determine if premature baboons with Hyaline Membrane Disease can be supported by the machine.

Eight baboons were delivered by sterile caesarean section at 137 to 143 days gestational age and were ventilated by the machine. 5 were 2 hour short term models and 3 were 24 hour models. The 2 hour models were ventilated at 15 Hz, 33% I and Power as required (12% to 85%). The 24 hour models were ventilated at 10 Hz, 33% I and power as required.

All of the animals survived and there were no malfunctions.

Optimum blood gas values and means proximal airway pressures are shown below for the 2 hour models comparing IPPV and HFV.

| Animal | PaCO$_2$ | PaO$_2$ (arterial pressure) | (A-aO2) alveolar O2 | arterial O2 | MAP |
|---|---|---|---|---|---|
| IPPV (Intermittent Positive Pressure Ventilation) | | | | | |
| Q | 31 | 213 | | 428 | 18 |
| R | 24 | 233 | | 417 | 13 |
| S | 38 | 119 | | 434 | 16 |
| T | 22 | 198 | | 455 | 13 |
| U | 41 | 184 | | 445 | 28 |
| AVG. | 31.2 | 189 | | 436 | 17.6 |
| HFV (High Frequency Ventilation) | | | | | |
| Q | 22 | 215 | | 437 | 11 |
| R | 31 | 214 | | 427 | 18 |
| S | 18 | 298 | | 360 | 16 |
| T | 38 | 248 | | 385 | 17 |
| U | 31 | 230 | | 411 | 14 |
| AVG. | 28 | 241 | | 404 | 15.2 |

Average arterial blood gases for the 2 hour models comparing IPPV and HFV ar shown below

| | IPPV | | | HFV | | |
|---|---|---|---|---|---|---|
| | PaO$_2$ | PaCO$_2$ | pH | PaO$_2$ | PaCO$_2$ | pH |
| Q | 127 | 40 | 7.09 | 103 | 29 | 7.29 |
| R | 97 | 36 | 7.25 | 141 | 24 | 7.31 |
| S | 92 | 47 | 7.04 | 214 | 29 | 7.35 |
| T | 140 | 31 | 7.32 | 162 | 45 | 7.15 |
| U | 115 | 46 | 7.16 | 145 | 36 | 7.19 |
| AVG | 114 | 40 | 7.17 | 153 | 33 | 7.26 |

Although the invention has been described in conjunction with the foregoing specific embodiment, many alternatives, variations and modifications are intended to fall within the spirit and scope of the appended claims.

What is claimed is:

1. An apparatus for supporting full ventilation in an air breathing animal comprising:
    means for supplying a respirating gas to an animal at elevated pressure,
    a linear motor,
    a diaphragm driven by said linear motor, and
    circuit means for producing a high frequency, variable frequency, variable amplitude signal for driving said linear motor to drive said diaphragm to generate a pressure wave in said gas which is polar relative to the static pressure in an airway of said animal, said pressure wave having a positively sloped portion forcing gas into said airway and a negatively sloped portion drawing gas out of said airway.

2. The apparatus of claim 1 wherein said gas supply means includes an outlet opening externally of said animal.

3. The apparatus of claim 2 wherein said gas supply means further comprises a valve in said opening adjustable to vary the elevated pressure in said gas supply means.

4. The apparatus of claim 1 wherein said circuit means comprises mans for driving said linear motor with a square wave signal.

5. The apparatus of claim 1 including means for independently varying the duration of the positively sloped portion of said pressure wave and the negatively sloped portion of said pressure wave.

6. The apparatus of claim 1 further comprising a volume ventilator connected to said gas supply means.

7. The apparatus of claim 1 including multiple sets of controls for controlling said pressure wave producing means and means for selectively switching from one set of said sets of controls to another set of said sets of controls, each of said sets of controls being operable to independently control said pressure wave producing means.

8. An apparatus for ventilating an air breathing animal comprising:
    a source of ventilating gas;
    means for connecting an air breathing animal to said source of ventilating gas having means therein for elevating the static pressure in said connecting means; and
    means in fluid connection with said connecting means for producing a high frequency pressure wave having a selected amplitude and frequency comprising a diaphragm in contact with said gas, a linear motor having an armature connected to said diaphragm, and circuit means including an oscillator and shaping circuitry for producing a high frequency polar output signal for driving said linear motor, said pressure wave producing means being operable to produce a pressure wave in said gas to force the gas in said connecting means into said animal and to draw the gas in said connecting means out of said animal.

9. The apparatus of claim 8 wherein said pressure wave producing means includes means for equalizing the pressure on opposite sides of said diaphragm to nullify the effect of the pressure on both sides of said diaphragm on the pressure wave produced by said pressure wave producing means.

10. The apparatus of claim 8 wherein said circuit means includes means for switching the frequency of said oscillator automatically between a first frequency and a second frequency.

11. The apparatus of claim 8 including a second oscillator for producing a second frequency output signal and means for superimposing said second frequency output signal on said high frequency output signal.

12. The apparatus of claim 8 including feedback means in said linear motor for producing a feedback signal indicative of the position of said armature.

13. An apparatus for supporting full ventilation in an air breathing animal comprising:
    means for producing a high frequency pressure wave in a respirating gas comprising
        a linear motor for driving a diaphragm,
        means for driving said linear motor with a square wave signal to produce a pressure wave in the respirating gas having a selected frequency and amplitude which is polar relative to a static airway pressure in an air breathing animal to be ventilated, and
    means for connecting said pressure wave producing means to the air breathing animal to be ventilated, said pressure wave being operable to draw respirating gas from the air breathing animal; and
    means for maintaining a positive static pressure in said connecting means.

14. The apparatus of claim 13 further comprising a volume ventilator connected to said connecting means.

15. The apparatus of claim 13 wherein said pressure wave producing means additionally comprises circuit means for driving said linear motor.

16. The apparatus of claim 15 wherein said pressure wave producing means includes means for equalizing the pressure on both sides of said diaphragm to nullify the effect of the pressure on both sides of said diaphragm on the pressure wave produced by said pressure wave producing means.

17. The apparatus of claim 13 further comprising means for exhausting respirating gas from said connecting means.

18. The apparatus of claim 17 wherein said exhaust means includes a valve for maintaining said positive static pressure in said connecting means.

19. An apparatus for ventilation of an air breathing animal comprising:
   means for producing a substantially continuous flow of gas;
   means for producing a square pressure wave of selected frequency and amplitude in said flow of gas for alternately exerting positive and negative pressure on said flow of gas; and
   means for connecting said pressure wave producing means to an air breathing animal including an exhaust for restricting said flow of gas to the atmosphere thereby maintaining an elevated static pressure in said connecting means, said pressure wave producing means being operable to cause the exchange of gas between said flow of gas and said air breathing animal.

20. The apparatus of claim 19 wherein said pressure wave producing means comprises a diaphragm, a linear motor for alternatively moving said diaphragm in one direction and then in the opposite direction, and circuit means for controlling the frequency of movement of said diaphragm.

21. The apparatus of claim 20 further comprising means for equalizing the pressure on both sides of said diaphragm.

22. The apparatus of claim 20 wherein said circuit means includes circuitry for moving said diaphragm a selected distance in one direction relative to the static position of said diaphragm and then back to said static position and beyond said static position by a selected distance.

23. The apparatus of claim 20 further comprising means for controlling the extent of movement of said diaphragm in both directions relative to the static position of said diaphragm.

24. The apparatus of claim 19 further comprising a volume ventilator in connection with said pressure wave producing means.

25. An apparatus for supporting full ventilation of an air breathing animal comprising:
   a signal generator for producing a square wave with a selected frequency and period;
   an amplifier for selectively varying the amplitude of said square wave;
   a polar converter for converting said amplified square wave to a polar amplified square wave;
   an airway tube;
   a substantially continuous flow of respirating gas through said airway tube;
   a diaphragm in contact with the gas in said airway tube;
   a linear motor for driving said diaphragm to alternately exert pressure against the gas in said airway tube in one direction and then exert pressure against the gas in said airway tube in the opposite direction in response to said polar amplified square wave so that the gas in said flow of respirating gas is exchanged with the gas in the lungs of an animal to be ventilated; and
   an exhaust for allowing the escape of gas from said airway tube to the atmosphere.

26. The apparatus of claim 25 wherein said diaphragm is mounted in an air tight chamber and said chamber is provided with means for connecting the sides of said chamber on both sides of said diaphragm.

27. A method of ventilating an air breathing animal comprising the steps of:
   supplying a flow of respirating gas to an air breathing animal to be ventilated at an elevated positive pressure;
   generating a polar pressure wave of selected amplitude and frequency to effect the exchange of the gas in the flow of respirating gas with the gas in the animal; and
   exhausting the flow of respirating gas to the atmosphere to ventilate the animal without the need for spontaneous breathing or additional ventilating devices.

28. The method of claim 27 wherein the positive pressure is maintained at a pressure below about 100 centimeters of water.

29. The method of claim 27 wherein said pressure wave is generated at a frequency of from 3 Hz to 50 Hz.

30. The method of claim 27 wherein said pressure wave is generated at a frequency from 5 Hz to 30 Hz.

31. The method of claim 27 wherein the period of said pressure wave is selectively variable.

32. The method of claim 27 including selectively varying the duration of the positive portion of said pressure wave relative to the negative portion of said pressure wave to vary the inspiration to expiration ratio.

33. The method of claim 32 wherein the inspiration to expiration ratio is set at a ratio of from about 80:20 to about 20:80.

34. The method of claim 32 wherein the inspiration to expiration ratio is set at a ratio of from about 70:30 to about 30:70.

35. The method of claim 32 wherein the inspiration to expiration ratio is changed while said pressure wave is being produced.

36. The method of claim 27 including producing a pressure wave at a second frequency and superimposing said second frequency pressure wave on said high frequency pressure wave.

37. The method of claim 27 including producing a pressure wave at a second frequency and switching between said high frequency pressure wave and said second frequency pressure wave at selected intervals.

38. The method of claim 37 wherein the frequency of said second pressure wave is relatively low and the amplitude of said second pressure wave is relatively high.

39. The method of ventilating an air breathing animal comprising supplying a substantially continuous flow of gas to an animal to be ventilated at elevated static pressure and alternately forcing gas into the animal and drawing gas out of the animal with a high frequency pressure wave in the flow of gas having a selected amplitude and frequency, said pressure wave having positively and negatively sloped portions whereby carbon dioxide from said animal and oxygen in the flow of gas are exchanged to ventilate the animal without the need for spontaneous breathing or additional ventilating devices.

40. The method of claim 39 further comprising exhausting the flow of gas to the atmosphere.

41. The method of claim 40 wherein the static airway pressure of the animal is elevated by restricting the flow of said gas to the atmosphere.

42. The method of claim 39 wherein said pressure wave is generated at a frequency of from about 3 Hz to about 50 Hz.

43. The method of claim 39 wherein said pressure wave is generated at a frequency of from about 5 Hz to about 30 Hz.

44. The method of claim 39 wherein the period of said pressure wave is selectively variable.

45. The method of claim 39 wherein the elevated static pressure is maintained below 100 cm $H_2O$.

46. The method of claim 39 wherein the elevated static pressure is maintained below 40 cm $H_2O$.

47. The method of claim 39 wherein the airway pressure of said animal is raised by from about 5 to about 15 cm $H_2O$ relative to the elevated static pressure during the positively shaped portion of said pressure wave.

48. The method of claim 39 wherein the airway pressure of said animal is lowered from about 5 to about 15 cm $H_2O$ relative to the elevated static pressure during the negatively shaped portion of said pressure wave.

49. The method of claim 39 including selectively varying the duration of the positively sloped portion of said pressure wave relative to the negatively sloped portion of said pressure wave to vary the inspiration to expiration ratio.

50. The method of claim 49 wherein the inspiration to expiration ratio is set at a ratio of from about 80:20 to about 20:80.

51. The method of claim 49 wherein the inspiration to expiration ratio is set at a ratio of from about 70:30 to about 30:70.

52. The method of claim 49 further comprising changing the inspiration to expiration ratio.

53. The method of claim 39 further including generating a pressure wave at a second frequency and superimposing said pressure wave of said second frequency on said high frequency pressure wave.

54. The method of claim 52 including switching between said high frequency pressure wave and said pressure wave of said second frequency at timed intervals.

55. The method of claim 54 including generating said pressure wave of said second frequency at a low frequency and high amplitude to produce a sigh.

56. The method of claim 39 wherein said continuous flow of ventilating gas is about 5 liters per minute.

* * * * *